United States Patent

Summers et al.

(10) Patent No.: US 9,427,357 B2
(45) Date of Patent: Aug. 30, 2016

(54) PREFORMED LENS SYSTEMS AND METHODS

(71) Applicant: AMO Development, LLC, Santa Ana, CA (US)

(72) Inventors: Dan Summers, Santa Clara, CA (US); Guang-ming Dai, Fremont, CA (US); Paul Bradford, San Jose, CA (US)

(73) Assignee: AMO Development, LLC, Santa Ana, CA (US)

( * ) Notice: Subject to any disclaimer, the term of this patent is extended or adjusted under 35 U.S.C. 154(b) by 0 days.

(21) Appl. No.: 13/773,913

(22) Filed: Feb. 22, 2013

(65) Prior Publication Data

US 2013/0237970 A1    Sep. 12, 2013

Related U.S. Application Data

(60) Provisional application No. 61/601,865, filed on Feb. 22, 2012.

(51) Int. Cl.
*A61B 18/18* (2006.01)
*A61F 9/008* (2006.01)
*A61F 9/009* (2006.01)
*A61B 18/20* (2006.01)

(52) U.S. Cl.
CPC .......... *A61F 9/00827* (2013.01); *A61F 9/009* (2013.01); *A61B 2018/2085* (2013.01); *A61F 9/008* (2013.01); *A61F 2009/00872* (2013.01)

(58) Field of Classification Search
CPC .................... A61F 9/008; A61F 2009/00872; A61B 2018/2085
USPC .......................................................... 606/4–6
See application file for complete search history.

(56) References Cited

U.S. PATENT DOCUMENTS

| | | | | |
|---|---|---|---|---|
| 5,549,632 | A * | 8/1996 | Lai .................................... | 606/5 |
| 2005/0107773 | A1* | 5/2005 | Bergt et al. ....................... | 606/4 |
| 2007/0219543 | A1* | 9/2007 | Yee .................................... | 606/5 |
| 2010/0036488 | A1* | 2/2010 | de Juan et al. .............. | 623/5.16 |
| 2010/0274228 | A1* | 10/2010 | Mrochen et al. ............. | 604/541 |
| 2013/0090634 | A1* | 4/2013 | Loden ............................... | 606/4 |

* cited by examiner

*Primary Examiner* — Lynsey Crandall
*Assistant Examiner* — Sebastian X Lukjan
(74) *Attorney, Agent, or Firm* — Abbott Medical Optics Inc.

(57) ABSTRACT

Embodiments of the present invention encompass the manufacture of pre-cut lenses and the use of such lenses in combination with laser surgical techniques, including femtosecond laser photodisruption or photoalteration treatments. These techniques further expand the capabilities of lasers, and allow their use for both incising and refractively altering the eye. In many instances, embodiments disclosed herein are suitable for the treatment or correction of regular refractive errors and an irregular refractive alterations (such as correcting an irregular refractive error of the eye), without having to resort to two separate laser systems.

6 Claims, 19 Drawing Sheets

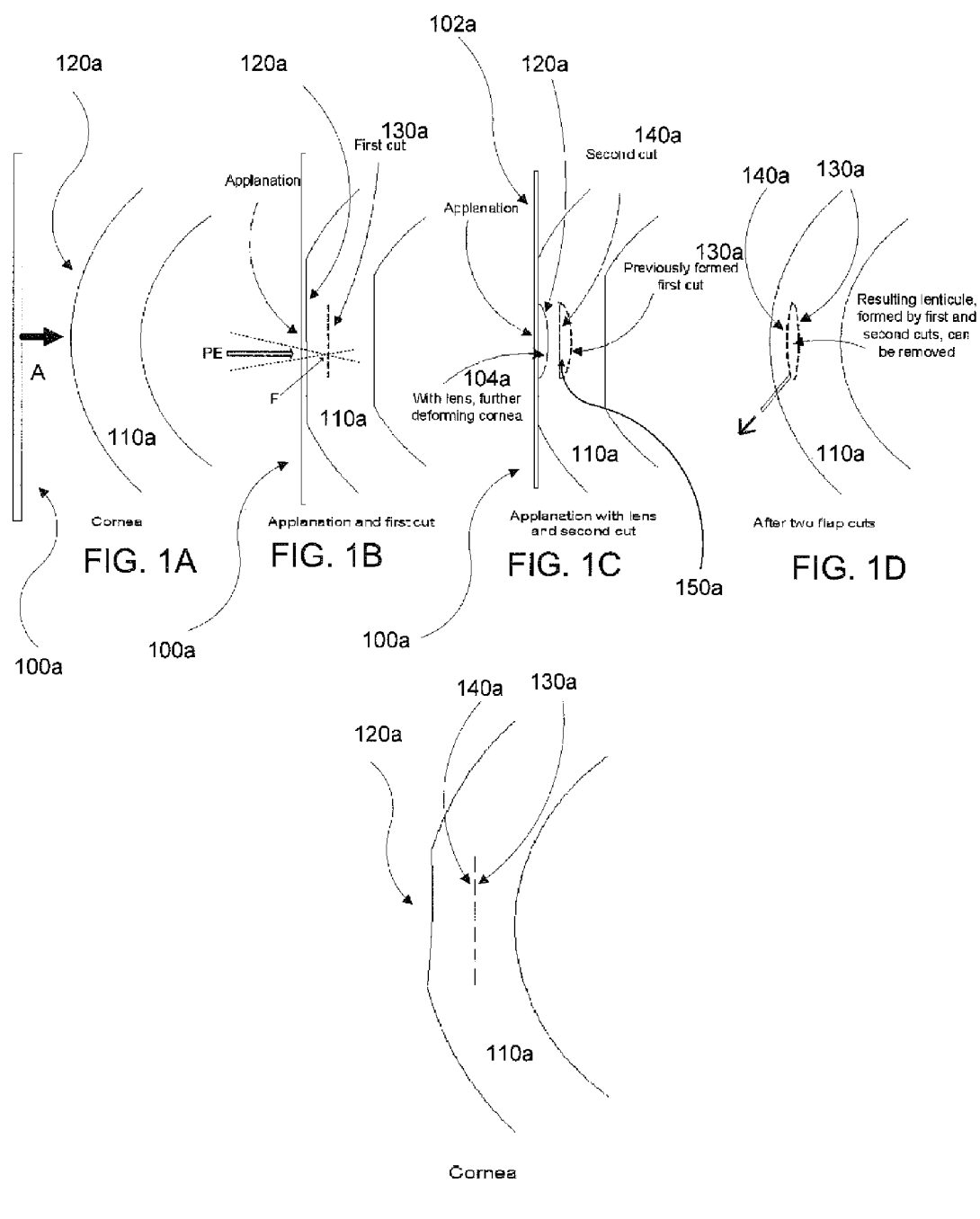

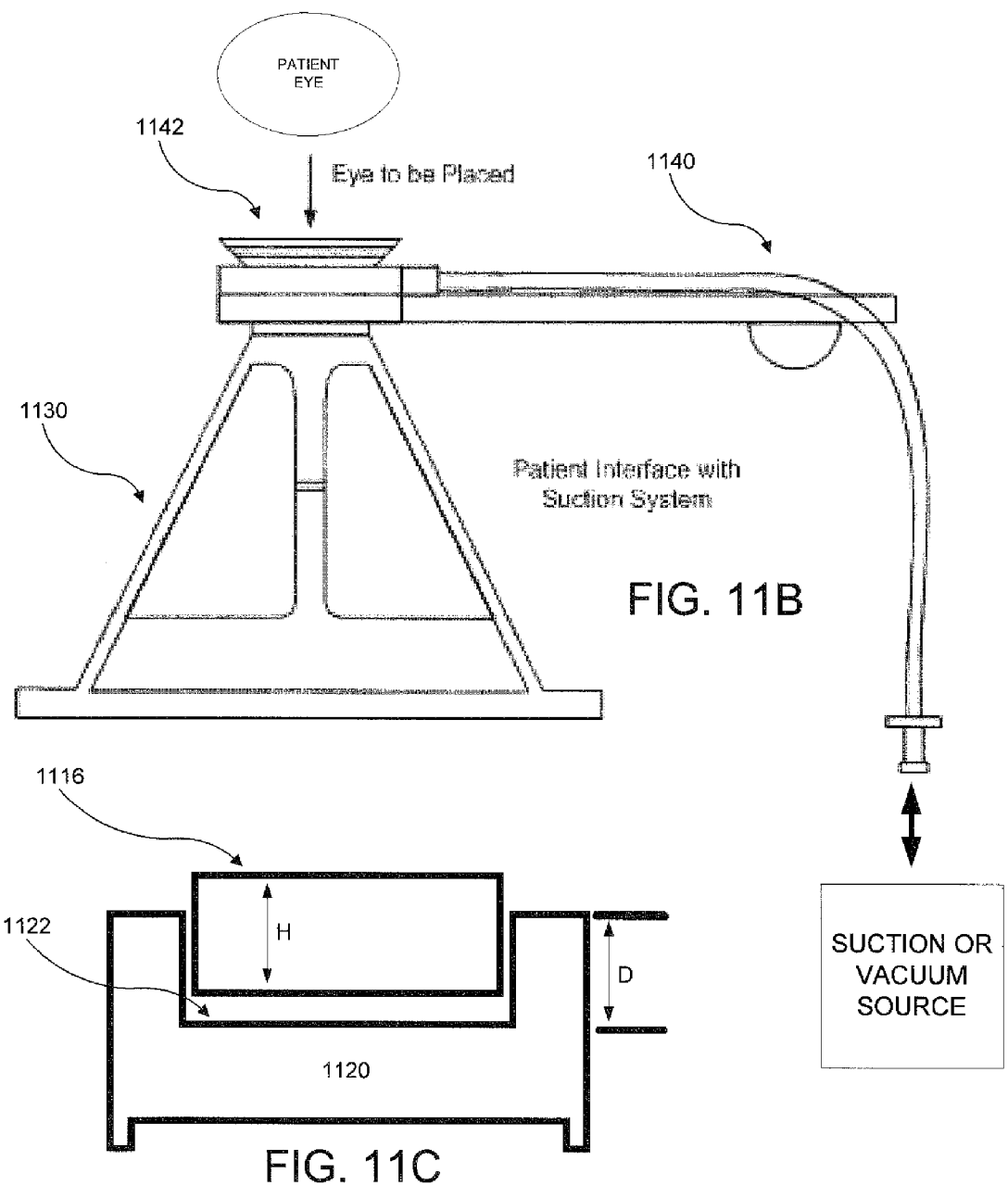

PREFORMED LENS SYSTEMS AND METHODS

CROSS-REFERENCES TO RELATED APPLICATIONS

This application claims priority to U.S. Application No. 61/601,865, filed on Feb. 22, 2012, which is related to U.S. patent application Ser. Nos. 11/677,504 and 12/471,090, filed Feb. 21, 2007 and May 22, 2009 respectively, the contents of which are incorporated herein by reference for all purposes.

BACKGROUND OF THE INVENTION

In general, embodiments of the present invention relate to the field of vision treatment. Exemplary embodiments relate to laser eye surgery devices, systems, and methods for selectively altering refractive properties of corneas having regular and/or irregular optical defects or shapes, often by directing energy into the corneal stroma.

Laser eye surgery systems and methods are now used to correct or treat defects in vision, often using a technique known as ablative photodecomposition. In general, this technique applies a pattern of laser radiation to an exposed corneal tissue so as to selectively remove and resculpt the cornea. The pattern of laser energy often includes a series of discrete laser pulses from an excimer laser, with the locations, sizes, and/or numbers of pulses of the pattern being calculated to achieve a desired volumetric resculpting of the cornea, and to thereby create enhanced optical properties or treat optical defects.

Many patients suffer from optical defects which are not easily treated using standard glasses and contact lenses. Glasses and contacts often treat only regular or spherical and cylindrical refractive errors of the eye. Wavefront diagnostic techniques have been developed to measure irregular refractive errors, and these techniques have proven highly useful in determining customized refractive prescriptions for these patients. The flexibility of laser photorefractive decomposition offers hope to these patients, as this technique can be used to resculpt the eyes to correct both regular and irregular refractive errors. By combining laser eye surgery techniques with wavefront diagnostic approaches, it is often possible to achieve visual acuity measurements of 20/20 or better for many patients.

Early laser eye surgery treatments often involved the removal of the epithelial layer before changing the shape of the underlying corneal tissue. The epithelial layer tends to regrow, whereas volumetric resculpting of the underlying stroma can provide long-lasting effects. Corneal resculpting techniques involving mechanical abrasion or laser ablation of the epithelial layer so as to expose the underlying stroma for volumetric photoablative decomposition are often referred to as photorefractive keratectomy ("PRK"), and PRK remains a good option for many patients. In the last several years, alternative techniques involving formation of a flap of corneal tissue (including the epithelial layer) have gained in popularity. Such techniques are sometimes popularly referred to "flap-and-zap," or laser in situ keratomileusis ("LASIK"). LASIK and related variations often have the advantage that vision can be improved within a few hours (or even minutes) after surgery is complete. LASIK flaps are often formed using mechanical cutting blades or microkeratomes, and the flap of epithelial tissue can be temporarily displaced during laser ablation of the stroma. The flap can reattach to the underlying stroma quite quickly, and the patient need not wait for epithelial tissue regrowth to experience the benefits of laser resculpting, so that these procedures are safe and highly effective for many patients.

A variety of alternative refraction altering techniques have also been proposed. In particular, focusing of femtosecond laser energy within the stroma so as to ablate a volume of intrastromal tissue has been proposed. By scanning the focal spot within an appropriate volume of the stromal tissue, it might be possible to vaporize the volume so as to achieve a desired refractive alteration. Despite possible advantages of intrastromal volumetric ablation techniques, these approaches have not yet gained the popularity of LASIK and/or PRK. Intrastromal femtosecond ablation techniques have, however, begun to gain popularity as a method for incising the cornea so as to form the flap of corneal tissue in LASIK and related procedures. Unfortunately, this combined approach often involves the use of both a fairly expensive intrastromal femtosecond laser for incising the corneal tissues, and then an excimer laser for resculpting the exposed stroma. The combined use of these two separate, fairly complex and/or expensive laser systems may limit the acceptability and benefits of these new refractive laser eye surgery techniques.

Hence, although current vision treatment modalities deliver real benefits to patients in need thereof, further advancement to provide to improved devices, system, and methods for laser eye surgery is desired. Embodiments of the present invention provide solutions that address certain inefficiencies or shortcomings which may be associated with known techniques, and hence provide answers to at least some of these outstanding needs.

BRIEF SUMMARY OF THE INVENTION

Embodiments of the present invention encompass the manufacture of pre-cut lenses and the use of such lenses in combination with laser surgical techniques, including femtosecond laser photodisruption or photoalteration treatments. These techniques further expand the capabilities of lasers, and allow their use for both incising and refractively altering the eye. In many instances, embodiments disclosed herein are suitable for the treatment or correction of regular refractive errors and an irregular refractive alterations (such as correcting an irregular refractive error of the eye), without having to resort to two separate laser systems.

Exemplary systems and methods involve the formation of two regular flap-type cuts or disruption patterns, where one pattern is formed using a pre-cut lens, and another pattern is formed without using the pre-cut lens. Tissue between the disruption patterns, which may be present as an envelope of a certain volume of stroma, can be removed, so as to alter the shape of the eye. In some cases, a femtosecond laser can be used to perform the photodisruption, thus providing an easy, precise, and effective approach to effective refractive surgery. Optionally, the photodisruption patterns can be created as a flat surface configuration. In some instances, the pre-cut lens includes a material having an index of refraction that matches the index of refraction of the corneal stroma. The pre-cut lens may be placed over the surface of the cornea, or onto a patient interface (PI). In some instances, the pre-cut lens can be manufactured according to principles used for the manufacture of intraocular lenses. By using the pre-cut lens, it is possible to provide spatially precise disruption patterns in such a way so as to avoid some of the difficulties that may be associated with other techniques for controlling a laser focal point in three dimensions to cut an envelope of tissue volume. For example, software control of arbitrary focusing of each laser pulse may be difficult to implement in certain situations. In contrast, the use of a preformed lens to create a flat surface disruption can be easier to implement. As noted elsewhere herein, by creating two cuts or disruption patterns (one using a preformed lens and one without using the lens), it is possible to define an amount of tissue for removal that approximates the volume and shape of the lens, thus leaving a void or space in the stroma that approximates the volume and shape of the lens.

The present invention generally provides improved devices, systems, and methods for laser eye surgery. In many embodiments, the invention will make use of femtosecond (or optionally picosecond) lasers and their ability to selectively ablate tissues within the cornea of an eye. By focusing energy from these lasers at a focal spot within a corneal stroma, and by scanning the spot along a surface, such lasers can quickly and accurately incise the corneal tissues along that surface. Rather than attempting to rely on volumetric intrastromal tissue vaporization, embodiments of the invention may largely (or even primarily) employ mechanical removal of tissues bordered by a laser incision surface. Advantageously, large variations in depth of the focal spot from a plane (or other surface, such as a sphere or the like) may be avoided by pre-shaping the corneal tissues using a tissue-shaping surface.

By selecting an appropriate tissue-shaping surface, for example based on a regular and/or irregular refractive error of the eye, and by calculating an appropriate tissue incision surface so as to correct or treat the regular and/or irregular errors, the corneal reshaping may mitigate both regular and irregular refractive defects. In some cases, the laser treatment may be completed in less than 100 seconds. In some cases, the treatment may be completed in less than 50 seconds. In some cases, the treatment may be completed in less than 30 seconds. In some cases, the treatment may be completed in less than 10 seconds. These time durations refer to the period of time between initiation of and completion of the laser ablation.

In some aspects, embodiments of the present invention provide systems and methods for altering refraction of an eye. For example, the eye may have a refractive error, and therefore may potentially benefit from receiving an optical treatment, the goal of providing a desired refractive alteration. In many embodiments, the desired refractive alteration of the eye may involve the correction of refractive defects, typically based on wavefront measurements of the eye. An appropriate tissue-shaping surface or deformation mechanism may be selected by choosing or manufacturing a shaping body, which can correspond to a desired refractive treatment for the eye. In exemplary embodiments, a tissue-shaping body may include a material transmissive of the laser energy used to form the spot. In many embodiments, tissue will be at least partially mechanically excised from between two disruption patterns. Tissue may be mechanically excised from between these two laser-formed or photoaltered tissue surfaces so that the eye has enhanced refractive characteristics when the two tissue surfaces engage each other, and without having to wait for epithelial regrowth.

In some aspects, embodiments may provide methods for customized correction of an eye. Exemplary methods may include measuring regular and/or irregular refractive errors of the eye. Aspects of the deformation mechanism or shaping body can be determined in response to the measured refractive error of the eye, and tissue of the eye can be incised by scanning a laser spot through the tissue along one or more laser target surfaces. Tissue bordered by the laser target surfaces can be mechanically excised so as to mitigate the regular and/or irregular refractive errors of the eye. In some cases, embodiments of the present invention encompass systems, kits, and computer program products for altering refraction of an eye.

In some aspects, embodiments provide a deformation mechanism or tissue-shaping body for use with a system to alter refraction of an eye. The eye will often have a refractive error, the system including a support for positioning the deformation mechanism or shaping body along an optical path from a laser and beam scanning optics for scanning along a target surface to incise tissue of the eye when the eye engages the body such that removal along the incised tissue surface mitigates the errors of the eye. The deformation mechanism or body may include a material transmissive of light from the laser, and a tissue shaping surface defined by the material.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in or in combination with alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom preformed lenses, intraocular lenses, custom contact lenses, custom corneal implants, and the like, which can be configured to treat or ameliorate any of a variety of vision conditions in a particular patient based on their unique ocular characteristics or anatomy.

In some instances, these techniques can be carried out in conjunction with treatments provided by any of a variety of laser devices, including without limitation the WaveScan® System and the STAR S4® Excimer Laser System both by Abbott Medical Optics Inc., the WaveLight® Allegretto Wave® Eye-Q laser, the Schwind Amaris™ lasers, the 217P excimer workstation by Technolas PerfectVision GmbH, the Mel 80™ laser by Carl Zeiss Meditec, Inc., and the like.

In one aspect, embodiments of the present invention encompass methods for providing a surgical treatment to an eye of a patient. Methods may include, for example, positioning a corneal deformation mechanism against an anterior surface of the eye of the patient, so as to induce a first intended biomechanical conformation within a corneal stromal tissue of the eye, and delivering a first photoaltering energy protocol to the eye while the corneal stromal tissue is in the first intended biomechanical conformation, so as to incise the corneal stromal tissue along a first target surface. Methods may also include positioning the corneal deformation mechanism against the anterior surface of the eye of the patient, such that the corneal stromal tissue of the eye assumes a second intended biomechanical conformation different from the first intended biomechanical conformation, and delivering a second photoaltering energy protocol to the eye while the corneal stromal tissue is in the second intended biomechanical conformation, so as to incise the corneal stromal tissue along a second target surface different from the first target surface. Further, methods may include removing a portion of corneal stromal tissue bounded by the first and second target surfaces. According to some embodiments, the corneal deformation mechanism includes an applanation assembly that provides a first shape configuration and a second shape configuration, such that when in the first shape configuration, the applanation assembly is shaped to induce the first intended biomechanical conformation within the corneal stromal tissue, and when in the second shape configuration, the applanation assembly is shaped to induce the second intended biomechanical conformation within the corneal stromal tissue. In some cases, the corneal deformation mechanism includes an applanation plate and a removable body. The removable body may be constructed of a material having an index of refraction of about 1.377, for example. According to some embodiments, the removable body is removed from the applanation plate during the first positioning and delivering steps, and the removable body is coupled or engaged with the applanation plate and contacts the anterior surface of the eye during the second positioning and energy delivery steps. In some instances, the removable body is coupled or engaged with the applanation plate and contacts the anterior surface of the eye during the first positioning and energy delivery steps, and the removable body is removed from the applanation plate during the second positioning and delivering steps. The step of removing the portion of corneal stromal tissue may involve emulsifying the portion of corneal stromal tissue with an ultrasonic device. In some cases, the step of removing the portion of corneal stromal tissue involves aspirating the emulsified tissue. In some cases, the step of removing the portion of corneal tissue involves aspirating the portion of tissue through a corneal incision. Methods may also include removing a natural crystalline lens from the eye of the patient. Some methods may include replacing a natural crystalline lens of the eye of the patient with an artificial intraocular lens implant.

In another aspect, embodiments of the present invention encompass methods of providing a surgical treatment to an eye of a patient that include positioning an energy transmission assembly against an anterior surface of the eye of the patient, so as to induce a first intended biomechanical conformation within a corneal stromal tissue of the eye, and delivering a first photoaltering energy protocol through the energy transmission assembly to the eye while the corneal stromal tissue is in the first intended biomechanical conformation, so as to incise the corneal stromal tissue along a first target surface. Methods may also include positioning the energy transmission assembly against the anterior surface of the eye of the patient, such that the corneal stromal tissue of the eye assumes a second intended biomechanical conformation different from the first intended biomechanical conformation, and delivering a second photoaltering energy protocol through the energy transmission assembly to the eye while the corneal stromal tissue is in the second intended biomechanical conformation, so as to incise the corneal stromal tissue along a second target surface different from the first target surface. Further, methods may include removing a portion of corneal stromal tissue bounded by the first and second target surfaces. According to some embodiments, the energy transmission assembly provides a first shape configuration and a second shape configuration, such that when in the first shape configuration, the energy transmission assembly is shaped to induce the first intended biomechanical conformation within the corneal stromal tissue, and when in the second shape configuration, the energy transmission assembly is shaped to induce the second intended biomechanical conformation within the corneal stromal tissue. In some cases, the energy transmission assembly includes an applanation plate and a removable body. The removable body may be constructed of a material having an index of refraction of about 1.377, for example. According to some methods, the removable body is removed from the applanation plate during the first positioning and delivering steps, and the removable body is coupled or engaged with the applanation plate and contacts the anterior surface of the eye during the second positioning and energy delivery steps. In some cases, the removable body is coupled or engaged with the applanation plate and contacts the anterior surface of the eye during the first positioning and energy delivery steps, and the removable body is removed from the applanation plate during the second positioning and delivering steps. According to some embodiments, the step of removing the portion of corneal stromal tissue includes emulsifying the portion of corneal stromal tissue with an ultrasonic device. According to some embodiments, the step of removing the portion of corneal stromal tissue includes aspirating the emulsified tissue. According to some embodiments, the step of removing the portion of corneal tissue includes aspirating the portion of tissue through a corneal incision. Some methods may include removing a natural crystalline lens from the eye of the patient. Relatedly, some methods may include replacing a natural crystalline lens of the eye of the patient with an artificial intraocular lens implant.

In yet another aspect, embodiments of the present invention encompass systems for altering refraction of an eye of a patient. For example, systems may include a corneal deformation mechanism configured to provide a first applanation shape configuration, and a second applanation shape configuration different from the first applanation shape configuration. Systems may also include a photoalteration laser for transmitting a laser beam along an optical path, a support for positioning the corneal deformation mechanism along the optical path, and a processor for determining a first laser target surface based on the first applanation shape configuration and a second laser target surface based on the second applanation shape configuration. Further, systems may include beam scanning optics coupled to the processor for scanning the beam along the first laser target surface when the eye assumes a first intended biomechanical conformation responsive to engagement with the first applanation shape configuration, and along the second laser target surface when the eye assumes a second intended biomechanical conformation responsive to engagement with the second applanation shape configuration. According to some embodiments, the corneal deformation mechanism may include a material having an index of refraction of about 1.377. In some instances, the corneal deformation mechanism may include an applanation plate having a substantially flat proximal portion for receiving the laser beam from the photoalteration laser, and a distal portion configured to engage an anterior corneal surface of the eye so as to induce the first intended biomechanical conformation in the eye. The corneal deformation mechanism may also include a lens deformation element having a proximal portion configured to engage the distal portion of the applanation plate, and a distal portion configured to engage the anterior corneal surface of the eye so as to induce the second intended biomechanical conformation in the eye. According to some embodiments, the distal portion of the applanation plate includes a substantially flat surface.

For a fuller understanding of the nature and advantages of the present invention, reference should be had to the ensuing detailed description taken in conjunction with the accompanying drawings.

BRIEF DESCRIPTION OF THE DRAWINGS

FIG. 1A illustrates aspects of optical treatment systems and methods according to embodiments of the present invention.

FIG. 1B illustrates aspects of optical treatment systems and methods according to embodiments of the present invention.

FIG. 1C illustrates aspects of optical treatment systems and methods according to embodiments of the present invention.

FIG. 1D illustrates aspects of optical treatment systems and methods according to embodiments of the present invention.

FIG. 1E illustrates aspects of optical treatment systems and methods according to embodiments of the present invention.

FIGS. 11A, 11B, and 11C depict aspects of surgical systems according to embodiments of the present invention.

DETAILED DESCRIPTION OF THE INVENTION

Figure 1:
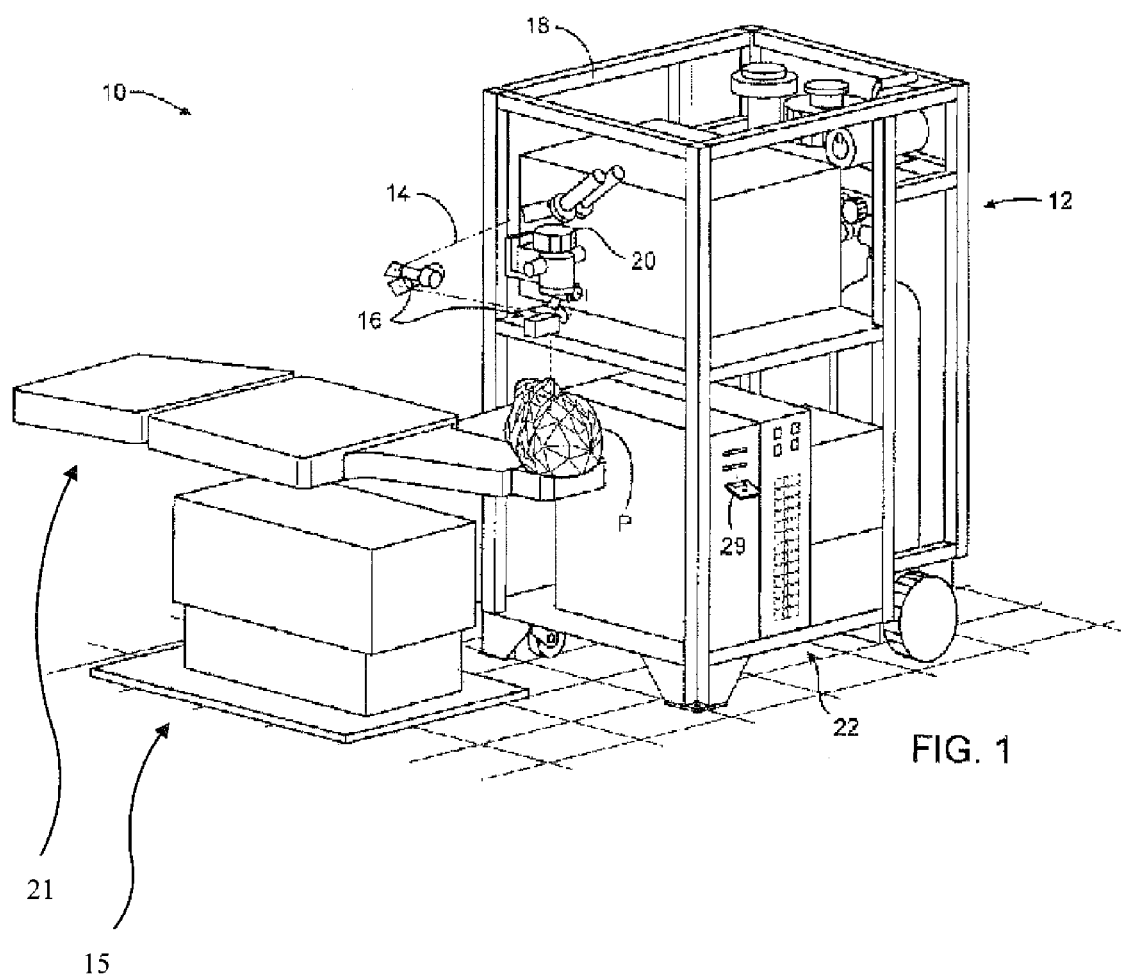
FIG. 1 is a schematic perspective view of a laser-eye surgery system and patient support system, according to embodiments of the present invention.

Embodiments of the present invention generally provides improved devices, systems, and methods for refractive correction of an eye. Embodiments of the invention can take advantage of the capabilities of femtosecond lasers, picosecond lasers and the like, to incise the eye along precisely defined target surfaces. In some instances, the volume of each individual laser ablation need not be precisely known and/or controlled, particularly when the total volume of tissue removal will be much greater than the overall volumetric ablation. Even when the absolute depth of an individual ablation or photoalteration is not perfectly controlled or known, focused intrastromal laser ablation or photoalteration may be able to incise the corneal tissue along a surface shape with sufficient accuracy (such as by controlling the depths of ablation or photoalteration spots along a target surface relative to each other) so as to provide a desired high order resculpting or reshaping of the overall cornea. By relying at least in part on incising and mechanical removal of tissues along the incised tissue surfaces (rather than solely or even primarily on volumetric photoablation), precise corrections may be provided very rapidly.

According to some embodiments, a femtosecond laser (or other laser) of the optical system can be used to incise the cornea or to cut a flap. A femtosecond laser may be used to make arcuate or other incisions in the cornea, which incisions may be customized, intrastromal, stable, predictable, and the like. Likewise, corneal entry incisions may be made, which are custom, multi-plane, and self sealing.

Many embodiments of the invention will make use of a selected corneal tissue-shaping surface, with the surface often being selected in response to a low-order, regular refractive error of the eye, and/or a high-order refractive error of the eye. By pre-shaping or conforming the tissue of the eye using a tissue-shaping surface that substantially corresponds to a regular and/or irregular refractive error of the eye, delivering photoaltering energy to the eye to incise the cornea along a first target surface, again conforming the tissue of the eye to that the eye assumes a second different confirmation, delivering a second photoaltering energy to the eye to incise the cornea along a second different target surface, and removing a portion of corneal tissue between the first and second target incisions, it is possible to reshape the cornea of the eye.

Exemplary embodiments of the invention include techniques for determining and manufacturing tissue-shaping bodies, with each body of the set corresponding to a standard refractive error or error range. By selecting or generating a body having an appropriate shape, and by conforming the tissue of the eye to the tissue shaping surface of that body, the capabilities of intrastromal laser ablations for correction of a wide range of regular and/or irregular refractive defects may be significantly enhanced.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use optionally in combination with alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom treatments which can be configured ameliorate any of a variety of vision conditions in a particular patient based on their unique ocular characteristics or anatomy.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 may comprises a femtosecond laser capable of providing pulsed laser beams, which may be used in optical procedures, such as localized photodisruption or photoalteration (e.g., laser induced optical breakdown). Localized photodisruptions or photoalterations can be placed at or below the surface of the material to produce high-precision material processing. For example, a micro-optics scanning system may be used to scan the pulsed laser beam to produce an incision in the material, create a flap of material, create a pocket within the material, form removable structures of the material, and the like. The term "scan" or "scanning" refers to the movement of the focal point of the pulsed laser beam along a desired path or in a desired pattern.

To provide the pulsed laser beam, the laser 12 may utilize a chirped pulse laser amplification system, such as described in U.S. Pat. No. RE 37,585, for photoalteration. U.S. Pat. Publication No. 2004/0243111 also describes other methods of photoalteration. Other devices or systems may be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point. Typically, photodisruption or photoalteration involves the disruption or optical tissue, such as corneal stroma or epithelium, ionization of molecules which is induced by the laser. In some cases, a short duration, high intensity laser is applied with low pulse energies, to form plasma and tissue disruption or optical breakdown at the laser focal point, often with minimal mechanical and thermal effects to nearby tissue, thus providing a precise cutting mechanism.

The system 10 is capable of generating the pulsed laser beam 14 with physical characteristics similar to those of the laser beams generated by a laser system disclosed in U.S. Pat. No. 4,764,930, U.S. Pat. No. 5,993,438, or the like. For example, the system 10 can produce a non-UV, ultrashort pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 14 has a wavelength that permits the pulsed laser beam 14 to pass through the cornea without absorption by the corneal tissue. The wavelength of the pulsed laser beam 14 is generally in the range of about 3 microns to about 1.9 nm, preferably between about 400 nm to about 3000 nm, and the irradiance of the pulsed laser beam 14 for accomplishing photodisruption of stromal tissues at the focal point is greater than the threshold for optical breakdown of the tissue. Although a non-UV, ultrashort pulsed laser beam is described in this embodiment, the laser 12 produces a laser beam with other pulse durations and different wavelengths in other embodiments.

In this embodiment, the delivery optics 16 direct the pulsed laser beam 14 toward the eye (e.g., onto the cornea) for plasma mediated (e.g., non-UV) photoablation of superficial tissue, or into the stroma for intrastromal photodisruption of tissue. The system 10 may also include an applanation lens (not shown) to flatten the cornea prior to scanning the pulsed laser beam 14 toward the eye. A curved, or non-planar, lens may substitute this applanation lens to contact the cornea in other embodiments.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser incising or sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired incisions or sculpting using a variety of alternative mechanisms. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference. In some cases, the laser beam 14 may be selectively limited using one or more variable apertures. An exemplary variable aperture system having a variable iris and a variable width slit is described in U.S. Pat. No. 5,713,892, the full disclosure of which is incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. Further details of suitable systems can be found in commonly assigned U.S. Publication Nos. 20090247997 and 20090247998, the complete disclosures of which are incorporated herein by reference. Suitable systems also include commercially available femtosecond laser systems such as those manufactured and/or sold by Alcon, Technolas, Nidek, WaveLight, Schwind, Zeiss-Meditec, Ziemer, and the like. According to some embodiments, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Basis data can be further characterized for particular lasers or operating conditions, by taking into account localized environmental variables such as temperature, humidity, airflow, and aspiration. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference.

The delivery optics 16 may include a scanner that operates at pulse repetition rates between about 10 kHz and about 400 kHz, or at any other desired rate. In one embodiment, the scanner generally moves the focal point of the pulsed laser beam 14 through the desired scan pattern at a substantially constant scan rate while maintaining a substantially constant separation between adjacent focal points of the pulsed laser beam 14. The step rate at which the focal point of the laser beam 14 is moved is referred to herein as the scan rate. The scan rates may be selected from a range between about 30 MHz and about 1 GHz with a pulse width in a range between about 300 picoseconds and about 10 femtoseconds, although other scan rates and pulse widths may be used. Further details of laser scanners are known in the art, such as described, for example, in U.S. Pat. No. 5,549,632, the entire disclosure of which is incorporated herein by reference.

In one embodiment, the scanner utilizes a pair of scanning mirrors or other optics (not shown) to angularly deflect and scan the pulsed laser beam 14. For example, scanning mirrors driven by galvanometers may be employed where each of the mirrors scans the pulsed laser beam 14 along one of two orthogonal axes. A focusing objective (not shown), whether one lens or several lenses, images the pulsed laser beam 14 onto a focal plane of the system 10. The focal point of the pulsed laser beam 14 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.]

FIG. 1A shows a corneal deformation mechanism 100a and a patient cornea 110a having an anterior surface 120a. As shown here, deformation mechanism 100a can be advanced toward anterior surface 120a, in a direction as indicated by arrow A. In a method of providing a surgical treatment to the eye of the patient, the corneal deformation mechanism 100a can be positioned against the anterior surface 120a of the eye of the patient, so as to induce a first biomechanical conformation within a corneal stromal tissue of the eye, as depicted in FIG. 1B. For example, as shown here, the corneal deformation mechanism 100a impinges upon the anterior surface 120a, so as to flatten or reshape the anterior surface, thus deforming the corneal tissue 110a. Photoaltering energy, as indicated by arrow PE, can be delivered to the eye while the corneal stromal tissue 110a is in a first biomechanical conformation (e.g. in response to the applied deformation mechanism 100a), so as to incise the corneal stromal tissue along a first target surface 130a. In this way, a steady and exacting fluence can be scanned in the x-y plane within the corneal stroma. As shown here, the photoaltering energy can form a beam waist, focal point, or altering focus F, which when scanned through the corneal tissue, for example as part of a first photoaltering energy protocol, creates an incision within the corneal tissue 110a along target surface 130a. The location or position of the focal point within the corneal stroma is governed by the applanated lens. In this way, the focal depth of the photoalteration within the eye is due to the external applanated lens which creates a deformation in the cornea, or otherwise imposes a desired biomechanical shape on the eye. As shown here, focus F can be scanned approximately parallel to a flat portion of the deformed flat anterior corneal surface 120a, in a way that the z axis depth of the focal point does not vary as the focus is scanned in the x-y plane. In addition to providing a photoalteration along a flat surface, embodiments of the present invention also encompass techniques for incising the eye along other types of predetermined paths, including surfaces with a consistent curvature, and the like.

As indicated in FIG. 1C, the corneal deformation mechanism 100a impinges upon the anterior corneal surface, so as to reshape the anterior surface and induce a second biomechanical conformation in the eye. In some cases, the corneal deformation mechanism 100a may be provided as an applanation assembly, which may include, for example, a first deformation element 102a (e.g. an applanation plate) and a second deformation element 104a (e.g. a lens). The corneal deformation mechanism 100a can be positioned against the anterior surface 120a of the eye of the patient, such that the corneal stromal tissue 110a of the eye assumes a second biomechanical conformation different from the first biomechanical conformation. As shown here, first incision 130a, which was a substantially flat incision in the conformation of FIG. 1B, has now become a curved incision in FIG. 1C. Photoaltering energy can be applied to the eye according to a second photoaltering energy protocol when the eye is in the second biomechanical conformation of FIG. 1C, so as to incise the corneal stromal tissue 110a along a second target surface 140a which is different from the first target surface 130a. Effectively, the presence of deformation element 104a operates to alter the depth of the focus of the femtosecond laser relative to the anterior corneal surface, by deforming the corneal tissue while at the same time not refracting the laser energy. In this way, a portion or volume 150a of corneal stromal tissue is defined between the first target surface 130a and the second target surface 140a. Again, formation of the second target surface 140a can be accomplished using a steady and exacting fluence of the laser, scanned in the x-y plane within the corneal stroma, in a way such that the z axis depth of the focal point does not vary during the scan.

The focal depth of the photoalteration within the eye is due to the external applanated lens which creates a deformation or biomechanical reshaping of the cornea, or otherwise imposes a desired biomechanical shape on the eye. In a first shape configuration (e.g. as depicted in FIG. 1B), the applanation assembly or deformation mechanism has a first pre-determined or known shape that is intended to induce a first biomechanical conformation within the corneal stromal tissue. In a second shape configuration (e.g. as depicted in FIG. 1C), the applanation assembly or deformation mechanism has a second pre-determined or known shape that is intended to induce a second biomechanical conformation within the corneal stromal tissue.

Embodiments of the present invention encompass systems and methods that involve the formation of a posteriorly disposed photoalteration or cut (e.g. incision along first target surface 130a) prior to the formation of an anteriorly disposed photoalteration or cut (e.g. incision along second target surface 140a), such as when the applanation plate is used in a first photoalteration step and the combined applanation plate and lens are used in a second photoalteration step following the first photoalteration step. Likewise, embodiments of the present invention similarly encompass systems and methods that involve the formation of an anteriorly disposed photoalteration or cut (e.g. incision along second target surface 140a) prior to the formation of a posteriorly disposed photoalteration or cut (e.g. incision along first target surface 130a), such as when the combined applanation plate and lens are used in a first photoalteration step and the applanation plate is used in a second photoalteration step following the first photoalteration step.

As depicted in FIG. 1D, methods may also include removing the portion 150a of corneal stromal tissue (e.g. a lenticule) that is bound by or disposed between the first and second target surfaces 130a, 140a. In some cases, the corneal tissue portion or lentoid volume 150a is removed via a suction tube. In some cases, the tissue portion, which may in some cases include both epithelium and stroma, may be removed mechanically from the eye using other techniques, such as by grasping the tissue with micro forceps, displacing the tissue using a flow of fluid (either liquid or gas), grasping the tissue using a vacuum applied through a port in a deformation element or a hand-held implement, or the like.

When the tissue portion 150a is removed, the shape of the resulting space between the first and second target surfaces approximates that of the second deformation element 104a. In this way, the shape of the deformation element or preformed lens can be approximated or mimicked as a corresponding cavity within the stroma. In some cases, the applanated element 104a is a customized shape, designed specifically to treat a particular vision condition of the patient.

As illustrated in FIG. 1E, following removal of portion 150a, the first and second target surfaces 130a and 140a can then oppose one another to close the space therebetween, for example by the corneal stroma collapsing upon itself, and as such the corneal tissue 110a adopts an altered or corrected shape or configuration, relative to the original shape or configuration shown in FIG. 1A. The altered or corrected eye shape is thus informed by the original eye shape as well as the deformation lens shape. According to some embodiments, the effect of the volumetric removal can be approximated, predicted, or simulated by providing the patient with a contact lens having a shape which corresponds to the shape of the deformation lens.

Removal of this tissue can effect both high-order or irregular refractive correction and low-order or regular refractive correction of the eye. Appropriate tissue removal shapes may be determined using ray tracing or wavefront analysis, through empirical studies, and the like, and may in some cases reflect the anticipated epithelial regrowth from an incision formed along a target laser surface. The incision need not be complete when a deformation mechanism is retracted, as small remaining contact points can optionally be separated by pulling of the severed tissue body. In some cases, the tissue targeted for removal may extend to an exposed tissue region engaged by the deformation mechanism, and a vacuum port of the deformation mechanism may be used to remove the tissue bordered by the incisions when the deformation mechanism is withdrawn proximally away from eye. Additional ports in the deformation mechanism (or an adjacent structure of the system) may provide fluid or gas flow to help separate the corneal tissues from the tissue-shaping surfaces and the like, to apply a vacuum to affix the engaged eye relative to the delivery optics, and the like. In some cases, deformation mechanism may include multiple tissue-shaping surfaces, such as a first tissue-shaping surface corresponding to a first selected shape, a second selected shape, and so on. Switching between the tissue-shaping surfaces may be implemented using the motion stages of a support structure.

Techniques developed to facilitate formation of a LASIK flap, including the formation of ablation reservoirs, applanation lens support and vacuum tissue affixation systems, alternating locations along the target surface to inhibit thermal damage, and the like, may be modified for use in laser incising of the corneal tissues along the target surface. Hence, as depicted in FIG. 1E, following removal of the lenticule or tissue portion, the tissues bordered by the laser target surfaces 130a and 140a can engage and attach to each other. Once again, the final corneal surface will reflect any regular and/or irregular or high-order aberration corrected provided by the deformation mechanism, but without here having to wait for epithelial regrowth to enjoy the benefits of the procedure. However, in contrast to standard LASIK procedures which involve the formation of such a hinged flap (e.g. partial microkeratome cut which is pulled back to expose the corneal bed, followed by volumetric ablation with an excimer laser, and replacement of the flap), embodiments of the present invention provide for the removal of a portion of the corneal stroma, without requiring creation of the hinged flap.

According to some embodiments, a method of providing a surgical treatment to an eye of a patient may include delivering a first photoaltering energy protocol through a first configuration laser transmitting assembly 100a, and into corneal stromal tissue 110a of the eye, so as to incise the corneal stromal tissue along a first target surface 130a, as shown in FIG. 1B. The first configuration laser transmitting assembly determines a first focal depth pattern (relative to the anterior corneal surface) for the delivered energy along the first target surface 130a. The method also includes delivering a second photoaltering energy protocol through a second configuration laser transmitting assembly 102a, 104a, and into corneal stromal tissue 110a of the eye, so as to incise the corneal stromal tissue along a second target surface 140a, as shown in FIG. 1C. The second configuration laser transmission assembly determines a second focal depth pattern (relative to the anterior corneal surface) for the delivered energy along the second target surface 140a. As depicted in FIG. 1D, the first target surface 130a corresponds to a first focal depth pattern (relative to the anterior corneal surface) and the second target surface 140a corresponds to a second focal depth pattern (relative to the anterior corneal surface). The difference between the first and second focal depth patterns corresponds to a resulting of portion of corneal stromal tissue disposed between the first and second target surfaces, which can be removed.

According to some embodiments, a method of providing a surgical treatment to an eye of a patient may include providing a first configuration energy transmitting assembly 100a along a beam path between an energy source and an anterior surface of the eye of the patient, and delivering a first photoaltering energy protocol along the beam path from the energy source, through the first configuration energy transmitting assembly, and into corneal stromal tissue 110a of the eye, so as to incise the corneal stromal tissue along a first target surface 130a, as shown in FIG. 1B. The first configuration energy transmitting assembly determines a first focal depth pattern (relative to the anterior corneal surface) for the delivered energy along the first target surface 130a. The method may also include delivering a second photoaltering energy protocol along the beam path from the energy source, through a second configuration energy transmitting assembly 102a, 104a, and into corneal stromal tissue 110a of the eye, so as to incise the corneal stromal tissue along a second target surface 140a, as depicted in FIG. 1C. The second configuration energy transmitting assembly determines a second focal depth pattern (relative to the anterior corneal surface) for the delivered energy along the second target surface 140a. As depicted in FIG. 1D, the first target surface 130a corresponds to a first focal depth pattern (relative to the anterior corneal surface) and the second target surface 140a corresponds to a second focal depth pattern (relative to the anterior corneal surface). The difference between the first and second focal depth patterns corresponds to a resulting of portion of corneal stromal tissue disposed between the first and second target surfaces, which can be removed.

Hence, embodiments of the present invention encompass systems and methods for providing a patient with an ocular treatment. Exemplary embodiments encompass techniques where the cornea is applanated and a laser light focal waist from a femtosecond laser beam is scanned laterally within eye in order to create a first incision, the cornea is further applanated, this time by including an inserted or auxiliary lens, and a femtosecond beam waist is used to create a second incision, such that the first and second cuts define a volumetric lenticule that can be removed, for example via suction through a needle, thus providing a reshaped cornea. According to some embodiments, the epithelium remains intact during the procedure. In this way, it is possible to remove a volume of corneal stromal tissue, without using complicated control mechanism to vary the z-axis depth of the beam focal point. Instead, the focal point of the beam is simply scanned across a flat or smooth surface when making both the first and the second cuts. In other words, two regular flap-type cuts can be made, where the first cut is made without the lens (e.g. a pre-cut IOL-like body), and the second cut is made using the lens. The volume of tissue removed is often determined by the shape of the lens or deformation mechanism used. Hence, that lens can be formed based on measured refractive properties of the eye, and the lens shape also corresponds to the refractive correction intended for the eye. Because the lens shape is being used to deform the cornea in a corresponding shape, and not necessarily to bend light, the lens material will often have a refractive index similar to that of the corneal stroma (e.g. 1.377). In some cases, material used in the fabrication of the lens can be selected so as to provide a consistent index of refraction between the lens, or interface lens system, and the eye.

According to some embodiments, a single cut extending through the epithelium can be made, when using the deformation mechanism or lens to deform the eye. In this way, the depth of the incision relative to the anterior surface of the cornea can be altered based on the shape of the deformation mechanism or lens. Because this technique can remove an amount of corneal surface epithelium, the procedure may involve a longer recovery time due to corneal healing or re-epithelialization.

According to some embodiments, a shaped lens can be used to adjust the depth of the beam waist relative to the anterior corneal surface. In some cases, however, the shaped lens may not be contacted with the cornea. Instead, the lens may operate to adjust the depth of the beam waist within the cornea, according to the lens shape.

Figure 1F:
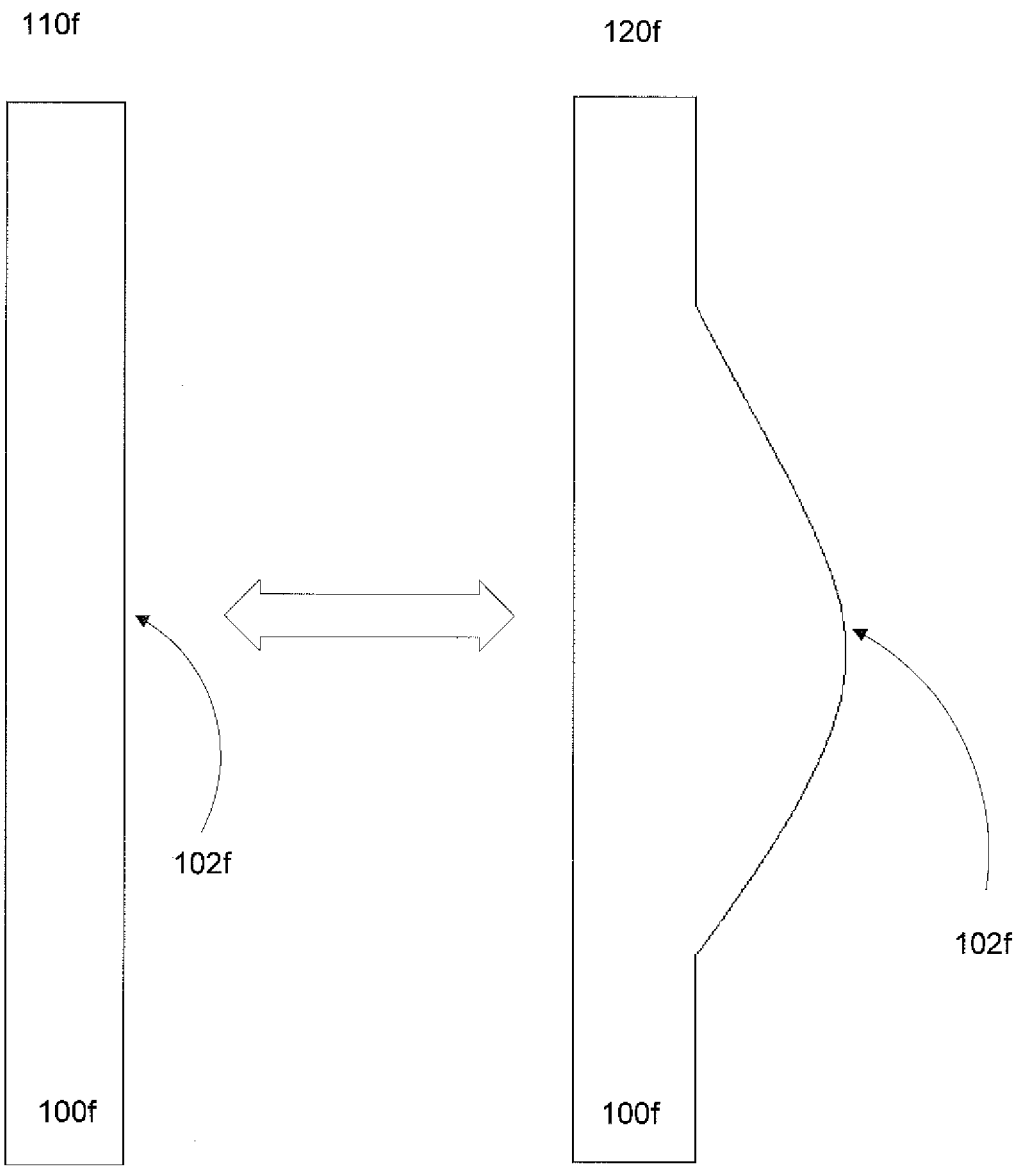
FIG. 1F illustrates aspects of optical treatment systems and methods according to embodiments of the present invention.

In some instances, an applanation assembly can transition between a first shape configuration and a second shape configuration. For example, as shown in FIG. 1F, applanation assembly 100f can modulate or change between a first shape configuration 110f and a second shape configuration 120f. When in the first shape configuration 110f, the applanation assembly 100f is shaped to induce a first biomechanical conformation within corneal stromal tissue when impinging or pressed thereupon (e.g. when a corneal contacting surface 102f of the assembly 100f is placed against the anterior corneal surface of the eye), and when in the second shape configuration 120f, the applanation assembly 100f is shaped to induce a second biomechanical conformation within corneal stromal tissue when impinging or pressed thereupon (e.g. when a corneal contacting surface 102f of the assembly 100f is placed against the anterior corneal surface of the eye).

Figure 1G:
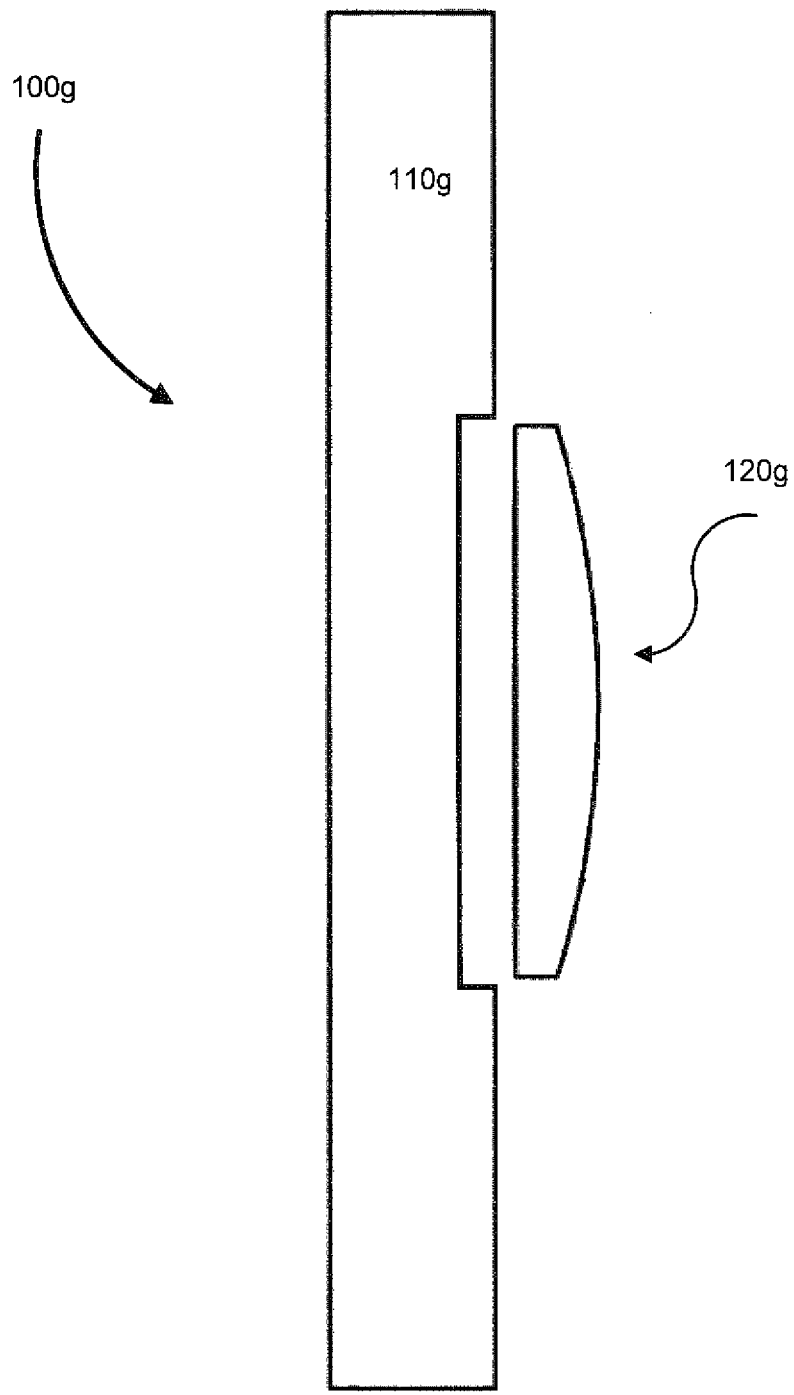
FIG. 1G illustrates aspects of optical treatment systems and methods according to embodiments of the present invention.

As shown in FIG. 1G, in some cases a corneal deformation mechanism 100g may include an applanation plate 110g and a removable body 120g. The removable body 120g may be attached to or detached from the applanation plate 110g. In some embodiments, the removable body 120g can be constructed of a material having an index of refraction of about 1.377. In some instances, deformation mechanism 100g may be used in a dual mode procedure. For example, in a first mode, the removable body 120g can be removed from the applanation plate 110g during one step (e.g. where the applanation plate 110g is positioned against the cornea, and photoalteration energy is delivered therethrough to the corneal tissue to form an incision) such that photoalteration energy passes through only the applanation plate 110g before photoaltering the eye. In a second mode, the removable body 120g can be coupled with the applanation plate 110g during another step (e.g. where the removable body 120g is positioned against the cornea, and photoalteration energy is delivered through both the applanation plate 110g and the removable body 120g to the corneal tissue to form an incision) such that photoalteration energy passes through the combined plate 110g and body 120g before photoaltering the eye.

Figure 1H:
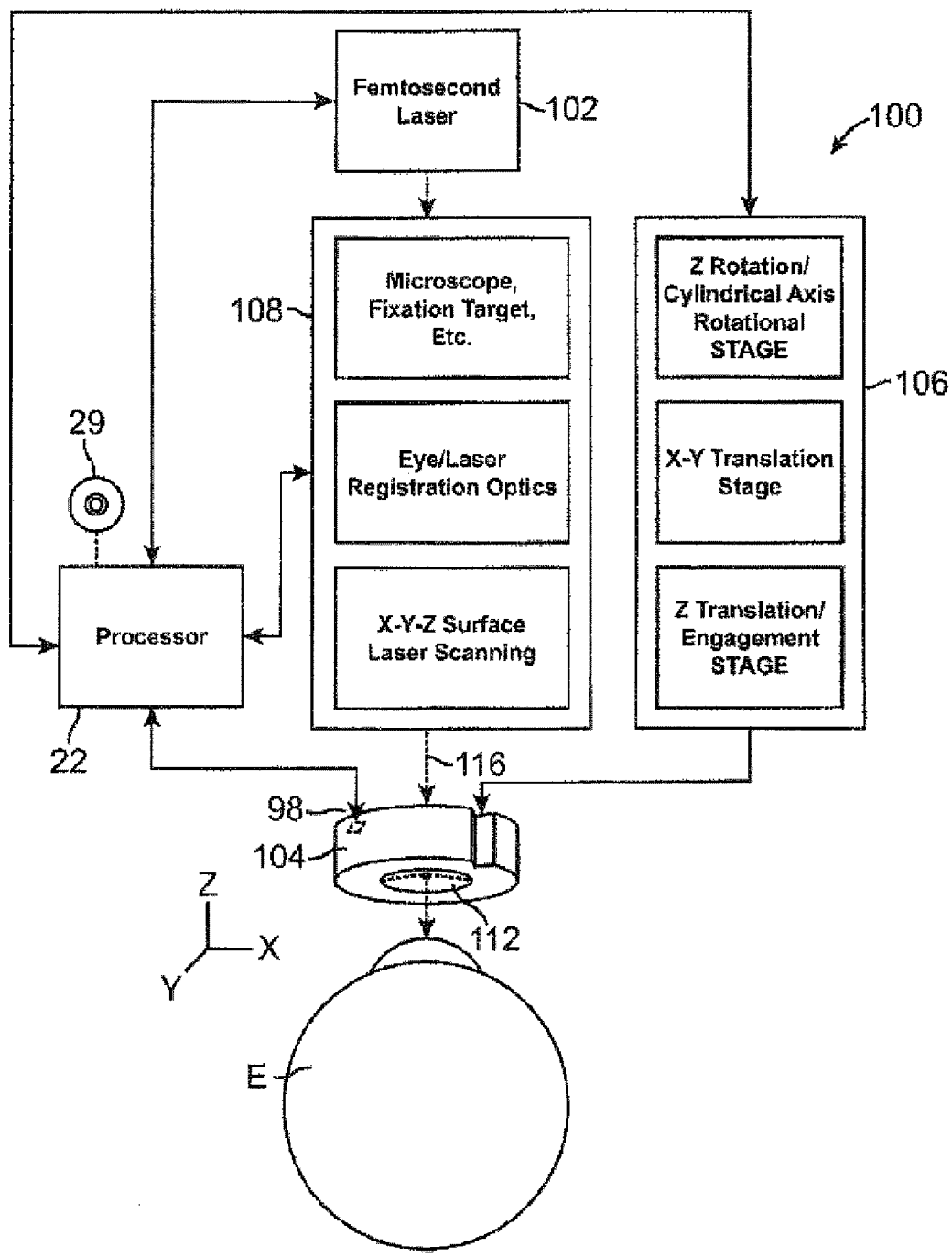
FIG. 1H illustrates aspects of optical treatment systems and methods according to embodiments of the present invention.

Referring now to FIG. 1H, an exemplary system 100 is suitable for correcting regular and/or and irregular refractive errors of eye E. System 100 generally directs laser energy from a femtosecond laser 102 to corneal tissues of eye E while those tissues are shaped by a deformation mechanism 104. In some cases, deformation mechanism 104 is supported and positioned by an electromechanical support structure 106, with the exemplary support structure having a series of motion stages for selectively positioning the deformation mechanism relative to the tissues of eye E. Optics 108 of system 100 selectively direct the laser energy from laser 102 into the corneal tissues, with the optics and support structure generally being under the control of a system processor or computer 22.

The deformation mechanism 104 generally includes at least one distal tissue-shaping surface 112. According to some embodiments, the target laser surface will, for example, be nominally planar, and the tissue-shaping surface may present a similarly nominally planar surface, or a shaped or curved surface. In an exemplary embodiment, a deformation mechanism may include a flat (or optionally curved or lens-shaped) proximal surface. The material along surface 112 (and typically from surface 112 to the proximal surface) comprises a material which is sufficiently transmissive of the laser energy from laser 102 to allow treatment eye E without overheating of the deformation mechanism, the tissue-shaping surface, and the engaged corneal tissues. Suitable materials may comprise, for example, glass, a suitable polymer such as PMMA, or the like. Deformation mechanism 104 may also include positioning surfaces that can be engaged by corresponding surfaces of the support structure 106 so as to accurately position the deformation mechanism horizontally (along the X-Y plane) relative to an optical axis 116 of the laser treatment, and also so as to rotationally position the deformation mechanism 104 about the axis 116 (such as the notch illustrated). This can help facilitate rotational alignment of any aspect of a tissue-shaping surface 112 relative to the eye E. A wide variety of alternative deformation mechanisms might also be implemented.

Referring now to FIG. 1H, elements of system 100 may be incorporated into, and/or may make use of components of a laser eye surgery system 10. Laser eye surgery system 10 generally includes a laser system 12 and a patient support system 15. Laser system 12 includes a housing that contains both a laser and a system processor 22. The laser generates the laser beam 14, which is directed to a patient's eye under the direction of a system operator. Delivery optics used to direct the laser beam, the microscope mounted to the delivery optics, and the like may employ existing structures from commercially available laser systems, including at least some portions of femtosecond or excimer refractive laser systems, such as those available from ADVANCED MEDICAL OPTICS, INC. of Santa Clara, Calif.

In addition to (or in some cases, instead of) adjustment to the delivery optics directing laser beam 14, alignment between the patient and the laser treatment system may be provided at least in part by the patient support system 15. Patient support system 15 generally includes a patient support 21 having an associated patient support movement mechanism. Patient support 21 may be contoured, helping to position the patient at a nominal location on the patient support. Large and fine adjustments of the patient support and patient may be effected using large and fine motion control mechanisms such as those more fully described in U.S. patent application Ser. No. 10/226,867 filed on Aug. 20, 2002, the disclosure of which is incorporated herein by reference.

Figure 2:
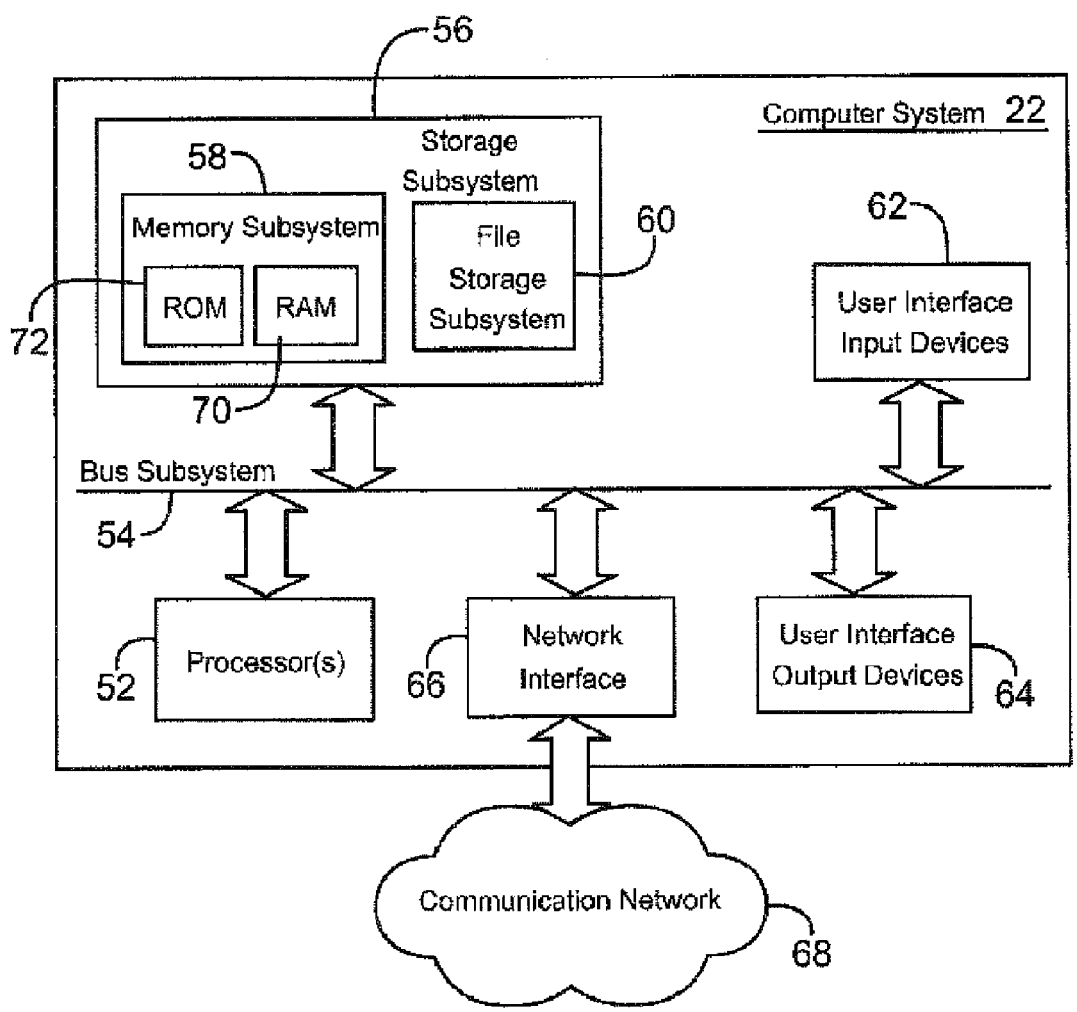
FIG. 2 is a schematic illustration of a data processing computer system for use in a laser eye surgery system, according to embodiments of the present invention.

FIG. 2 is a simplified block diagram of an exemplary computer system 22 that may be used by the laser surgical system 100. Computer system 22 typically includes at least one processor 52 which may communicate with a number of peripheral devices (and/or other processors) via a bus subsystem 54. These peripheral devices may include a storage subsystem 56, typically including a memory 58 and a file storage subsystem 60. The peripheral devices may also include one or more user interface input device 62, user interface output device 64, and a network interface subsystem 66. Network interface subsystem 66 can provide an interface to outside networks 68 and/or other devices, such as the wavefront measurement system 30 described below with reference to FIG. 3 or 3A.

User interface input devices 62 may include a keyboard, pointing devices such as a mouse, trackball, touch pad, or graphics tablet, a scanner, foot pedals, a joystick, a touch screen incorporated into the display, audio input devices such as voice recognition systems, microphones, and other types of input devices. User input devices 62 will often be used to download a computer executable code from a tangible storage media 29 embodying any of the methods described herein. In general, use of the term "input device" is intended to include a variety of conventional and proprietary devices and ways to input information into computer system 22.

User or user interface output devices 64 may include a display subsystem, a printer, a fax machine, or non-visual displays such as audio output devices. The display subsystem may comprise a cathode ray tube (CRT), a flat-panel display such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 stores the basic programming and data constructs that provide the functionality of the various embodiments of the invention. For example, a database and modules implementing the functionality of the methods described herein may be stored in storage subsystem 56. These software modules will generally be executed by processor 52. In a distributed processing environment, the software modules may be stored on any of a plurality of computer systems and executed by processors of those computer subsystems. Storage subsystem 56 typically comprises memory subsystem 58 and file storage subsystem 60.

Memory subsystem 58 typically includes a number of memories including a main random access memory (RAM) 70 for storage of instructions and data during program execution, and a read only memory (ROM) 72 in which fixed instructions are stored. File storage subsystem 60 may provide persistent (non-volatile) storage for program and data files, and may include tangible storage media 29 (see e.g. FIGS. 1, 1H, and 3) which may optionally embody wavefront sensor data, wavefront gradients, a wavefront elevation map, a treatment map, and/or an ablation table, as well as machine readable code or programming instructions for implementing the data processing and control methods described herein. File storage subsystem 60 may include a hard disk drive, a floppy disk drive (along with associated removable media), a compact digital read only memory (CD-ROM) drive, an optical drive, DVD, CD-R, CD-RW, solid-state removable memory, and/or other removable media cartridges or disks. One or more of the drives may be located at remote locations or on other connected computers at other sites coupled to computer system 22. The modules implementing the functionality of embodiments of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although a single bus subsystem is shown schematically, alternate embodiments the bus may utilize multiple bus systems or multiple busses.

Computer system 22 can be of various types including a personal computer, a portable computer, a work station, a computer terminal, a network computer, a control system in a wavefront measurement system or laser surgical system, a mainframe, or another appropriate data processing system. As computers and networks change over time, the description of computer system 22 shown in FIG. 2 represents only an example for purposes of illustration of an embodiment of the invention, and many other configurations of computer systems are possible, for example system configurations having more or less components than the computer system depicted in FIG. 2.

As noted above, laser system 100 may correct both regular and irregular optical errors of the eye. Regular optical errors (such as spherical errors associated with myopia and hyperopia, and cylindrical errors associated with standard cylindrical stigmatism) can be measured using any of a wide variety of commercially available diagnostic devices, including phoropters, automated refractometers, trial lenses, and the like. While a variety of devices and systems have also been developed and to measure irregular optical errors of the eye (including topographers, tomography systems, and the like) any irregular astigmatism or high-order aberrations of the eye will often be measured using a wavefront system.

Figure 3:
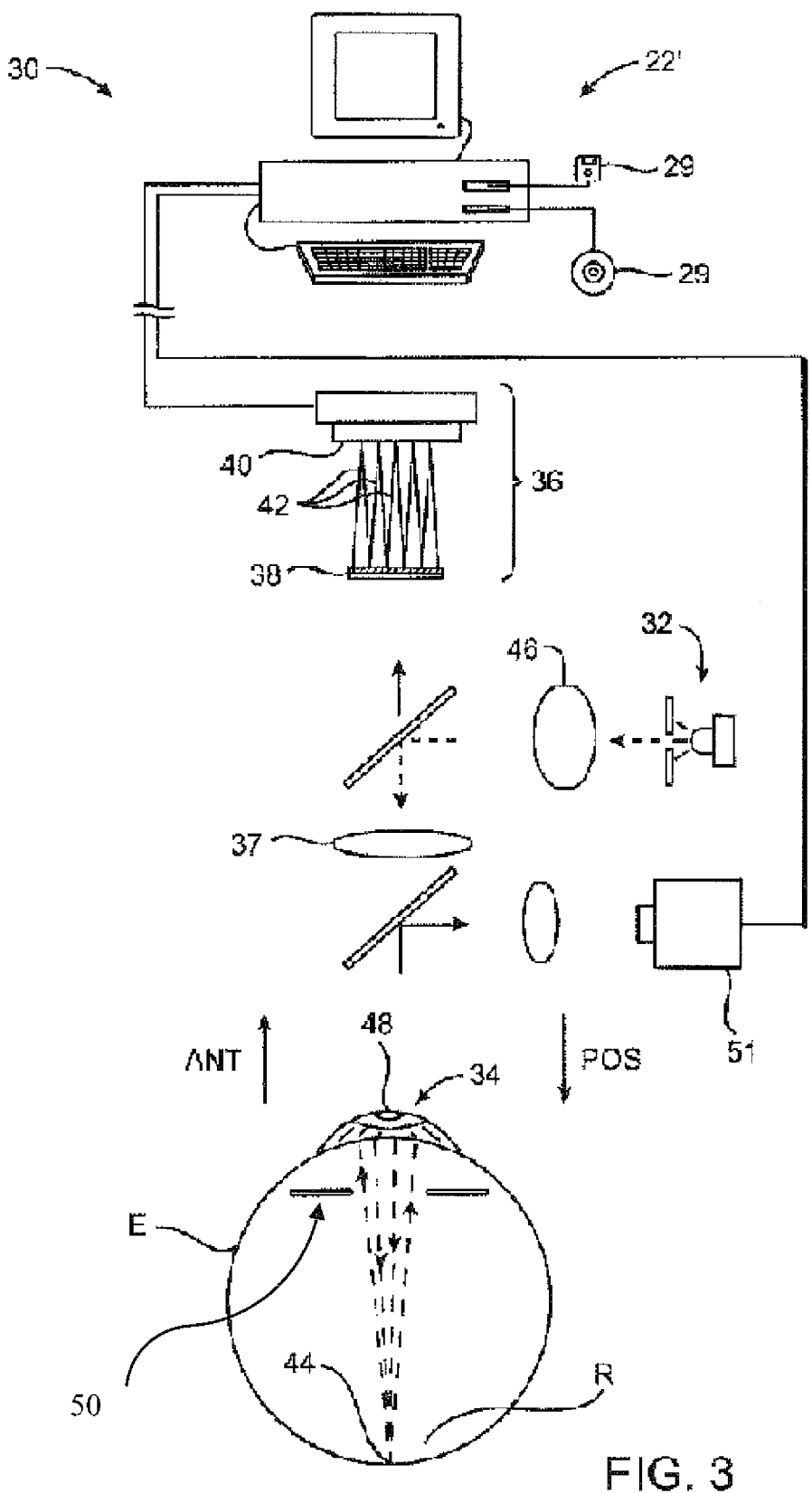
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a wavefront exiting the patient's eye. Devices based on the Hartmann-Shack principle generally include a lenslet array to sample the slopes across the pupil of the eye. In some embodiments, lenslet arrays may be used to sample the gradient map uniformly over an aperture, which is typically the exit pupil of the eye. Thereafter, the local slopes, for example of the gradient map, are analyzed so as to reconstruct the wavefront surface or map, often using Zernike polynomial expansion methods.

More specifically, one wavefront measurement system 30 includes a light or image source 32, such as a laser, which projects a source image through optical or refractive tissues 34 of eye E so as to form an image 44 upon a surface of retina R. The image from retina R is transmitted by the optical or refractive system of the eye (e.g., optical or refractive tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1, 1H, and 2. Computer system 22' may be in communication with computer system 22 that directs the laser surgery system 10, or some or all of the computer system components of the wavefront measurement system 30 and laser surgery system 10 may be combined or separate. If desired, data from wavefront sensor 36 may be transmitted to a laser computer system 22 via tangible media 29, via an I/O port, via a networking connection 66 such as an intranet or the Internet, or the like.

Wavefront sensor 36 generally comprises a lenslet array 38 and an image sensor 40. The reflected light from retina R is transmitted through optical tissues 34 and imaged onto a surface of image sensor 40 and the eye pupil P is similarly imaged onto a surface of lenslet array 38. The lenslet array separates the transmitted light beam into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image or light source 32 generally sends light in a posterior orientation through optical tissues 34 onto retina R as indicated in FIG. 3. Optical tissues 34 again transmit light or image 44 reflected from the retina anteriorly toward wavefront sensor 36. Image 44 actually formed on retina R may be distorted by any imperfections in the eye's optical system when the image source is originally transmitted by optical tissues 34. Optionally, image projection optics 46 may be configured or adapted to decrease any distortion of image 44.

In some embodiments, projection optics or image source optics 46 may decrease lower order optical errors by compensating for spherical and/or cylindrical errors of optical tissues 34. Higher order optical errors of the optical tissues may also be compensated through the use of an adaptive optics system, such as a deformable mirror. Use of a light source or image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular light source structure, it will be generally be beneficial to have a well-defined and accurately formed image 44 on retina R.

According to some embodiments, wavefront data may be stored in computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information may include the available information on the wavefront error of the eye and is typically sufficient to reconstruct the wavefront or a desired portion of it. In such embodiments, there may be no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While embodiments of the invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
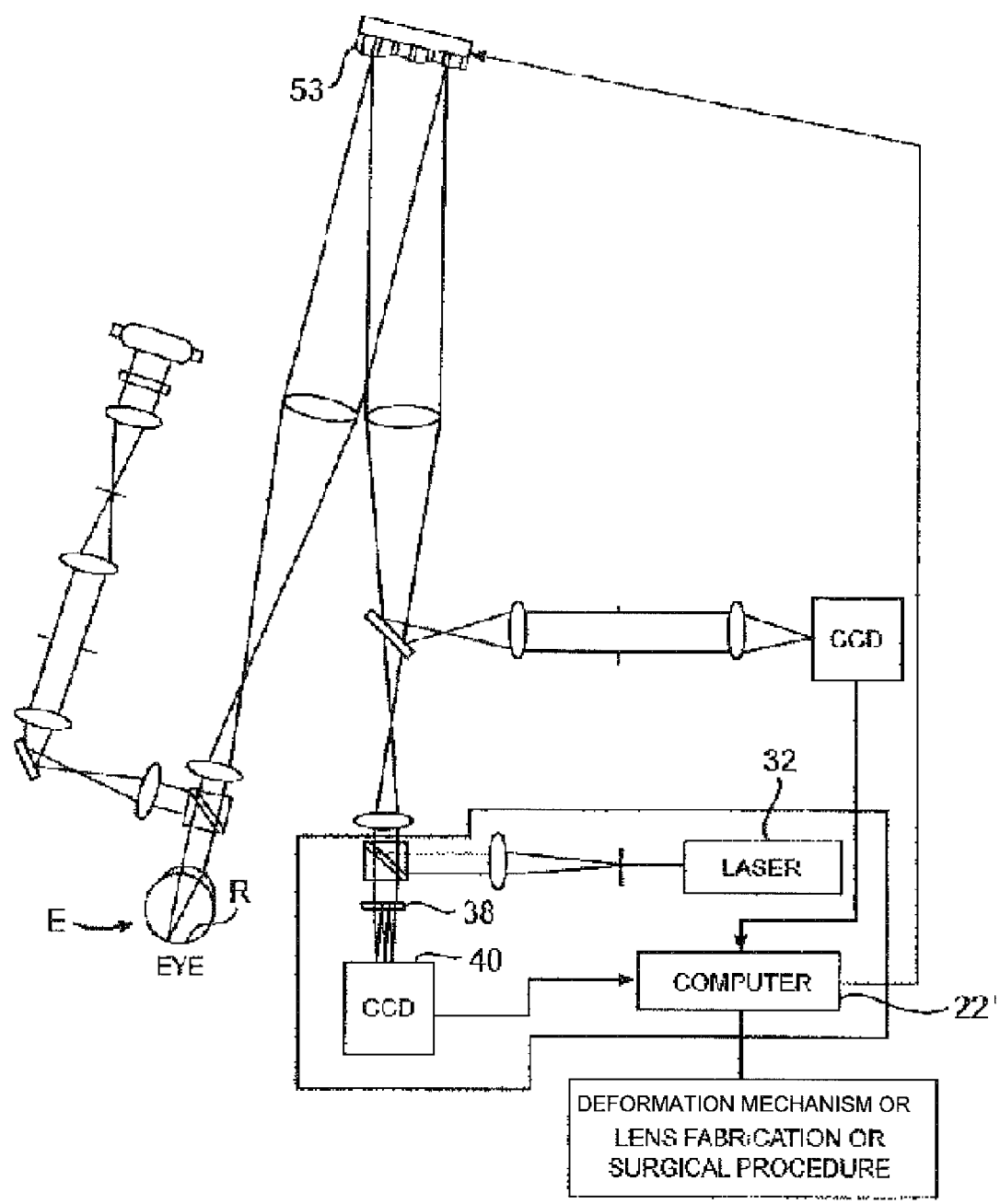
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO Manufacturing USA, LLC, Milpitas, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by AMO WaveFront Sciences, LLC, including the COAS wavefront aberrometer, the ClearWave contact lens aberrometer, the CrystalWave IOL aberrometer, and the like.

Figure 4:
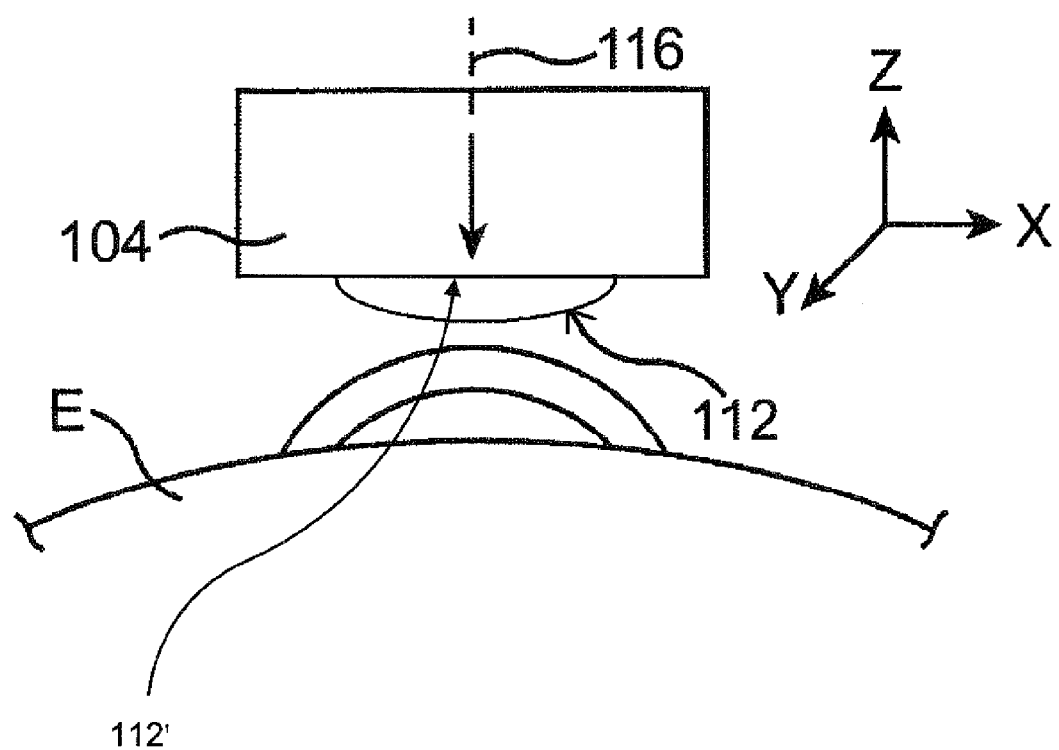
FIG. 4 is a schematic side view of a simplified model of an eye and tissue-shaping surface and body, according to embodiments of the present invention.
Figure 5:
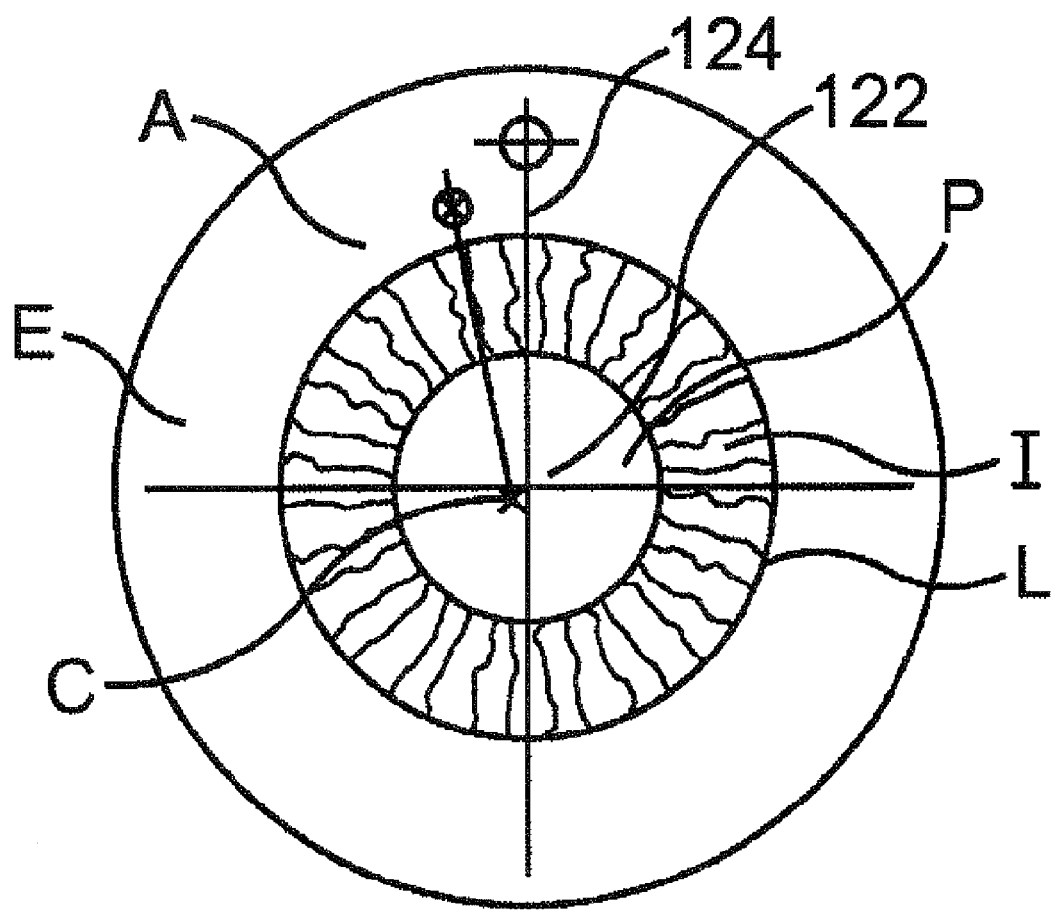
FIG. 5 is a schematic illustration of an image taken from along the optical path through the image shaping body of FIG. 4, showing horizontal and rotational alignment offsets between the tissue shaping body and tissues of the eye, as maybe identified using image processing software in the system of FIG. 1H, according to embodiments of the present invention.

Referring now to FIG. 4, treatment of eye E often begins by aligning body 104 with the eye. Body 104 will often be moved horizontally (in the X-Y plane) so as to align an optical axis 116 of the laser treatment system and tissue-shaping surface 112 or 112' with the corneal tissues. The eye may be imaged through body 104 as schematically illustrated in FIG. 5, and known image processing techniques can be used to identify a position and orientation of the eye with reference to a pupil P, features of the iris I, an outer edge of the iris or limbus L, or the like. Body 104 and/or eye E may be moved horizontally so as to align a center C of pupil P with a center 122 of surface 112 or 112'. Additionally, body 104 may be rotated about axis 116 so as to align an stigmatism axis A of eye E with a cylindrical axis 124 of surface 112 or 112'.

Positioning of the eye E relative to body 104 may be determined using a variety of methods and systems for tracking torsional orientation and position of an eye, including those described in U.S. Patent Publication No. US2003/0223037, the full disclosure for which is incorporated herein by reference. Such tracking techniques often make use of the striations in the iris I and the location of the pupil boundary for torsional and horizontal positioning, respectively. This information may be provided to the various motion stages of support system 106 (see e.g. FIG. 1H) to drive body 104 into alignment with the eye. Alternatively, the eye may be aligned with the axis 116 by relying, in at least some dimensions, upon fixation of the eye on a viewing target, with engagement between the tissue-shaping surface 112 or 112' into the eye occurring only when the alignment is within an acceptable range, such as when any alignment offsets are less than or equal to desired thresholds.

As described in additional details elsewhere herein, absolute alignment between positioning surface 112 or 112' and the tissue of the eye need not be provided. So long as the alignment is within an acceptable range, some adjustment of the effective location of the imposed refractive shape may be provided by adjusting the laser target surface. If the engagement between the tissue-shaping surface 112 or 112' and eye is sufficiently inaccurate that offsets (either horizontally, between pupil center C and surface center 122, or torsionally between astigmatism axis A and cylinder axis 124) exceeds a desired threshold, then the body 104 may be disengaged from the eye, the eye or the body repositioned, and the body again being advanced into engagement with the eye. This may continue until the alignment offsets are within the desired thresholds. The thresholds may be established so as to allow sufficient adjustment to the final refractive correction using changes to the laser target surface, so that the depth range of the laser target surface may effect the acceptable alignment offsets. Calculation of the laser target surface, and changes to the laser target surface so as to accommodate alignment offsets, may be implemented using any of a wide range of optical analytical tools that have been developed and commercialized, including those used for customized wavefront-based laser eye surgery and the like.

Once body 104 and the eye E are sufficiently aligned, the body is pressed against the corneal tissues of the eye so that the corneal tissues can form to the shape of surface 112 or 112'. The cornea need not conform to surface 112 or 112' throughout the entire tissue-shaping surface and/or cornea, so long as the cornea conforms to the desired shape throughout an optically used portion U of the corneal tissues of eye E. While the cornea conforms to surface 112 or 112', the laser energy from a laser can be focused at a spot, and the spot can be scanned along a target laser surface within the cornea.

Structures and methods for focusing and scanning the laser spot within the cornea so as to incise the corneal tissue are described in a variety of references, including U.S. Pat. Nos. 6,325,792 and 6,899,707, the contents of which are incorporated herein by reference. Laser systems and devices for forming incisions in the cornea using focused laser energy (often for use in LASIK procedures) may be commercially available from Abbott Medical Optics, Inc. and others. Known corneal laser incision techniques often incise the cornea along a plane, often while the corneal surface is applanated so as to form a thin epithelial flap of relatively constant thickness. Embodiments of the present invention will often vary the target laser surface from such a plane (or other standard surface shape, such as a sphere or the like). By conforming the corneal tissue to a desired shape such as by use of tissue-shaping surface 112 or 112', and by incising the cornea along a plane or other target surface, a desired refractive correction of the cornea can be effected.

Figure 6:
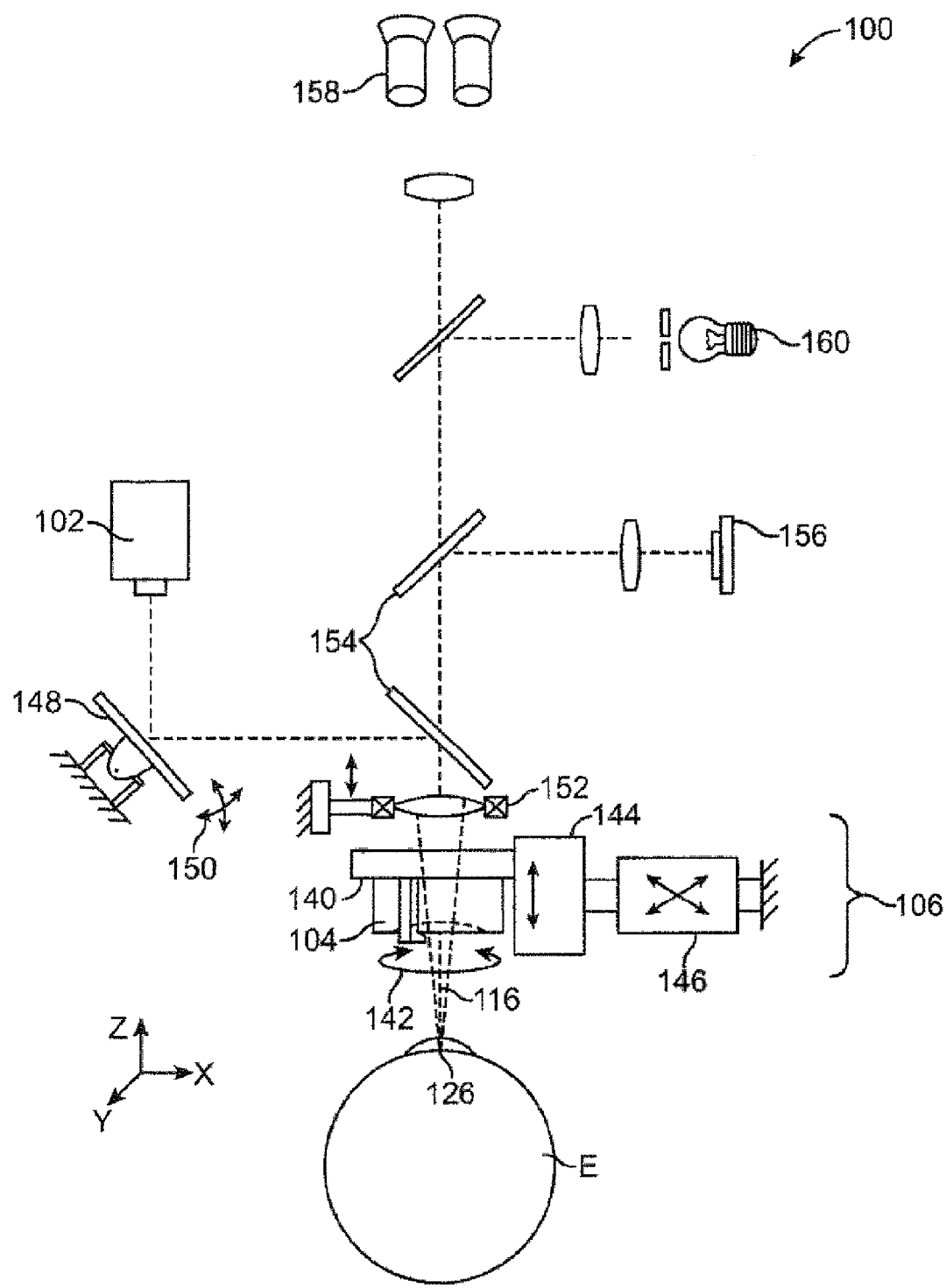
FIG. 6 schematically illustrates some of the optical and structural components of the laser system of FIG. 1H, according to embodiments of the present invention.

Referring now to FIG. 6, some of the optical and support system components are schematically illustrated. Shaping body or deformation mechanism 104 is mounted in a receptacle 140 having a rotational drive for rotating the shaping body about the axis 116, as indicated by arrows 142. Translation of shaping body 104 along axis 116 so as to engage the shaping body against eye E is provided by a Z axis translation/engagement motion stage 144, while horizontal positioning of the shaping body in the X-Y plane is effected using a two dimensional X-Y translation stage 146. In some embodiments, one or more of these motions may be manually effected, such as by having the system user preposition body 104 at an orientation appropriate for the patient's astigmatism axis.

To effect lateral scanning of the laser energy from laser 102, a two dimensional scanning mirror 148 optionally pivots in two dimensions, as indicated by arrows 150. Alternative arrangements may employ a first scanning mirror to scan the laser energy along the X axis, and a second scanning mirror having a pivot axis angularly offset from that of the first mirror may provide scanning primarily along the Y axis. Still further alternative scanning mechanisms may be employed, including X-Y translation of an offset imaging lens, and the like. Scanning of the laser spot 126 along axis 116 may be effected by movement of one or more focusing lens 152 along the optical path in between the laser and eye. As the scanning rate of the laser spot 126 within the tissue of the eye E may be quite rapid, it will generally be beneficial to minimize the weight of any electro mechanical scanning elements, drive the scanning elements with relatively high speed actuators such as galvanometers, and the like.

Many of the remaining optical and control components of system 100 may be similar to (or modified from) components of existing laser eye surgery systems. For example, the optical path may employ a series of beam splitters 154 to selectively direct portions of the light from eye E, optionally using wavelength-selective reflection. An image sensor 156 may capture an image of the eye through shaping body 104 and other components along the optical path, with the captured image often being used for establishing and/or verifying alignment between the eye and shaping body 104, laser spot 126, and other components of the optical path. Signals from the image sensor 156 may be used to identify a center of the pupil of eye E, a rotational orientation of eye E, and the like. Such signals may be used to drive the various motion stages of support structure 106 and movable optical components of optics 108 per calculations of processor 22 (see e.g. FIG. 1H). Images from image sensor 156 may also be used to measure alignments offsets and the like as described above. Images may also be displayed on a display screen of the laser eye surgery system, which may be used in conjunction with (or instead of) direct viewing of the procedure through binocular microscope 158. Additional optical and/or mechanical components of system 100 may also be included, including a fixation target 160, additional lenses and groups of lenses for processing the light on the optical path, and the like.

Figure 7A:
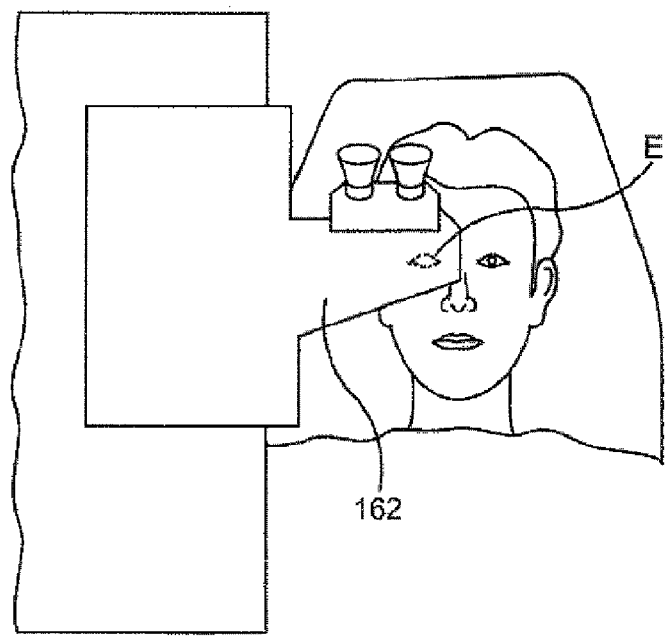
FIGS. 7A and 7B are top and side views, respectively, of a laser delivery arm of the system of FIG. 1H, according to embodiments of the present invention.
Figure 7B:
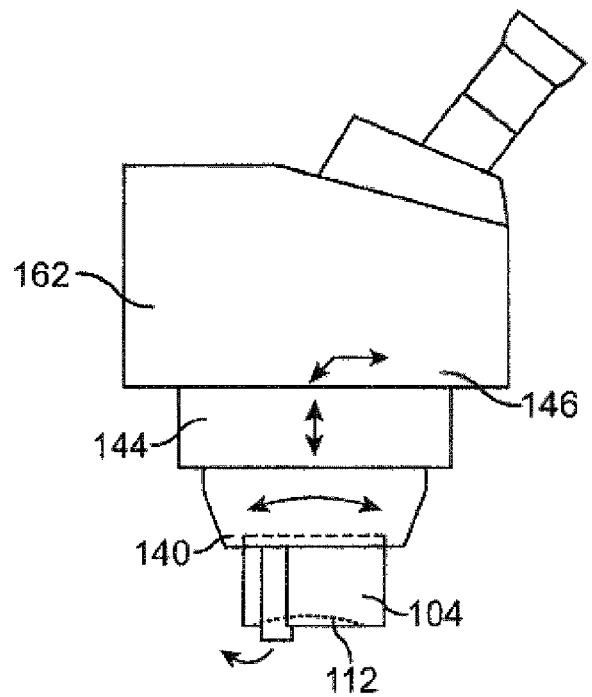

Referring now to FIGS. 7A and 7B, top and side views, respectively, of a support arm 162 show many of the components described above regarding support system 106. The rotational stage of receptacle 140, the axial translation stage 144, and the horizontal motion stage 146 may be arranged in a variety of differing orders, or may be combined or separated into fewer or more individual stages having different degrees of freedom in a wide variety of possible arrangements. The receptacle 140 can be configured to receive shaping body 104 and engage positioning surfaces of the shaping body so as to allow accurate positioning and rotation of the shape and body into alignment with the eye. While a simple latch of the receptacle is schematically illustrated, no structure of the receptacle will typically extend beyond the shaping body so as to interfere with engagement between the shaping surface 112 and the eye E. It should be noted that the incisions need not absolutely sever the tissues from the eye, as any relatively small remaining connection points may be detached by mechanical excision, such as by simply pulling the substantially severed tissues. After ablation or photoalteration along the target laser surface or surfaces is complete, shaping body 104 may be retracted away from the eye E and the desired tissue excised from along the one or more target laser surfaces 236.

Figure 8:
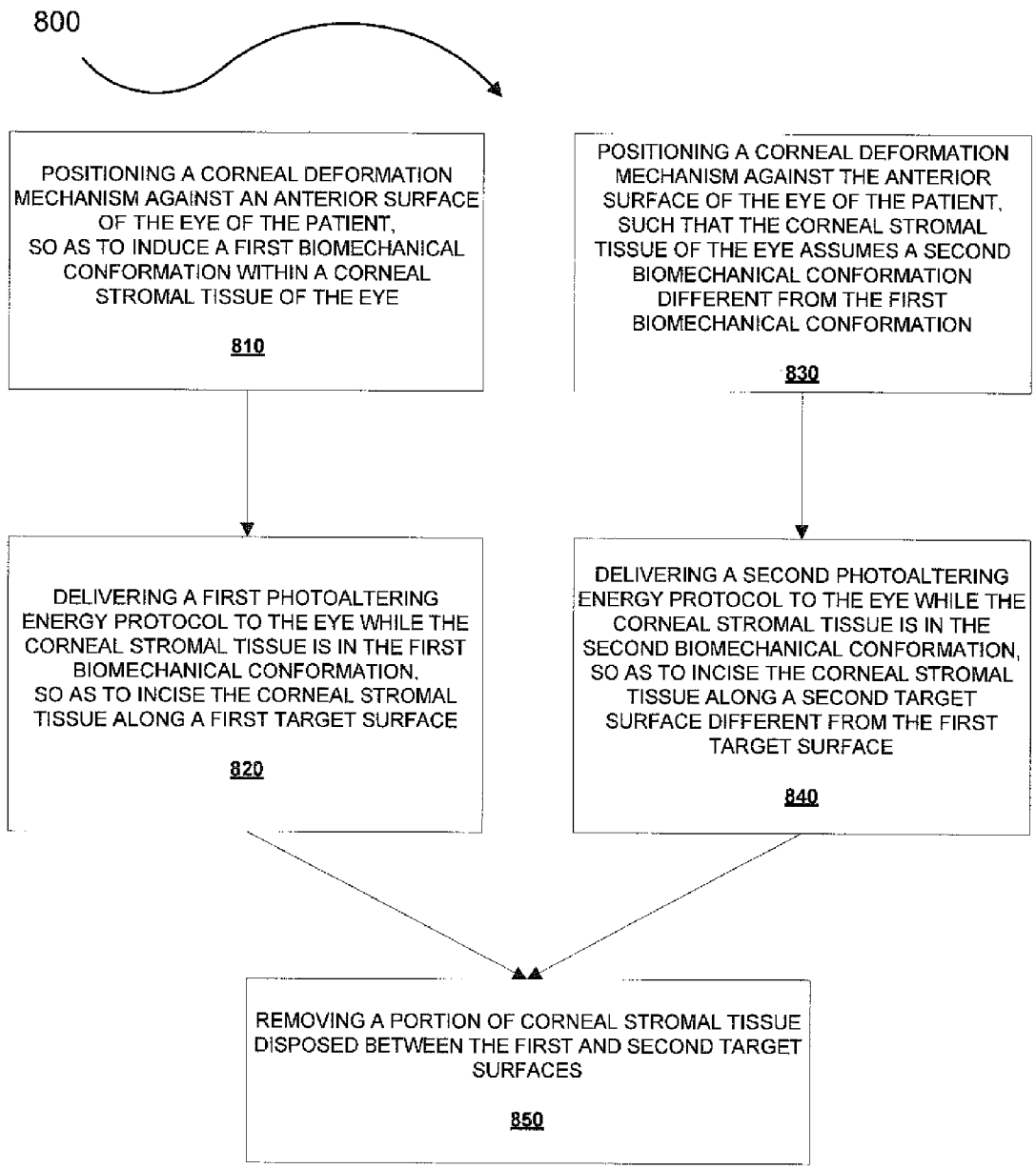
FIG. 8 depicts aspects of a treatment process according to embodiments of the present invention.

FIG. 8 depicts aspects of a method for providing a surgical treatment to an eye of a patient, according to embodiments of the present invention. As illustrated here, method 800 includes positioning a corneal deformation mechanism against an anterior surface of the eye of the patient, so as to induce a first biomechanical conformation within a corneal stromal tissue of the eye, as shown by step 810. Method 800 also includes delivering a first photoaltering energy protocol to the eye while the corneal stromal tissue is in the first biomechanical conformation, so as to incise the corneal stromal tissue along a first target surface, as shown by step 820. Further, method 800 includes positioning a corneal deformation mechanism against the anterior surface of the eye of the patient, such that the corneal stromal tissue of the eye assumes a second biomechanical conformation different from the first biomechanical conformation, as shown by step 830. Method 800 also includes delivering a second photoaltering energy protocol to the eye while the corneal stromal tissue is in the second biomechanical conformation, so as to incise the corneal stromal tissue along a second target surface different from the first target surface, as shown by step 840. What is more, method 800 includes removing a portion of corneal stromal tissue disposed between the first and second target surfaces, as depicted by step 850.

According to some embodiments, the corneal deformation mechanism may include an applanation assembly. For example, the applanation assembly may provide a first shape configuration and a second shape configuration, such that when in the first shape configuration, the applanation assembly is shaped to induce the first biomechanical conformation with the corneal stromal tissue, and when in the second shape configuration, the applanation assembly is shaped to induce the second biomechanical conformation within the corneal stromal tissue. In some cases, the corneal deformation mechanism may include an applanation plate and a removable body. The removable body may be constructed of a material having an index of refraction of about 1.377, for example. In some instances, the removable body may be removed from the applanation plate during the first positioning and delivering steps. Optionally, the removable body may be coupled with the applanation plate, and may contact the anterior surface of the eye during the second positioning and energy delivery steps.

After the tissue volume is removed, and as the cornea heals, the effect of the photoalteration flap cuts is in some cases similar to that of an excimer-laser ablated tissue removal, and thus the photoalteration technique can produce an equivalent or substantially equivalent effect to that of refractive surgery with excimer lasers. According to some embodiments, it is helpful to select the lens or deformation mechanism material such that it is very close, if not identical, to that of the corneal stroma, i.e., 1.377. The creation, or manufacturing, of the lens or deformation mechanism can be similar or identical to that used for the development of normal intraocular lenses. Hence, the manufacturing process may include aspects of molding, polishing, measuring of the power, quality control, and the like, which are similar or identical to processes used for the manufacture of intraocular lenses. According to some embodiments, spherical lenses of deformation mechanisms with given discrete values can be pre-made and used to deform the corneal tissue during a treatment. Toric lenses can also be made in a similar way. According to some embodiments, customized lenses or deformation mechanisms can be made, which consider low order aberrations, high order aberrations, and combinations thereof.

Figure 9:
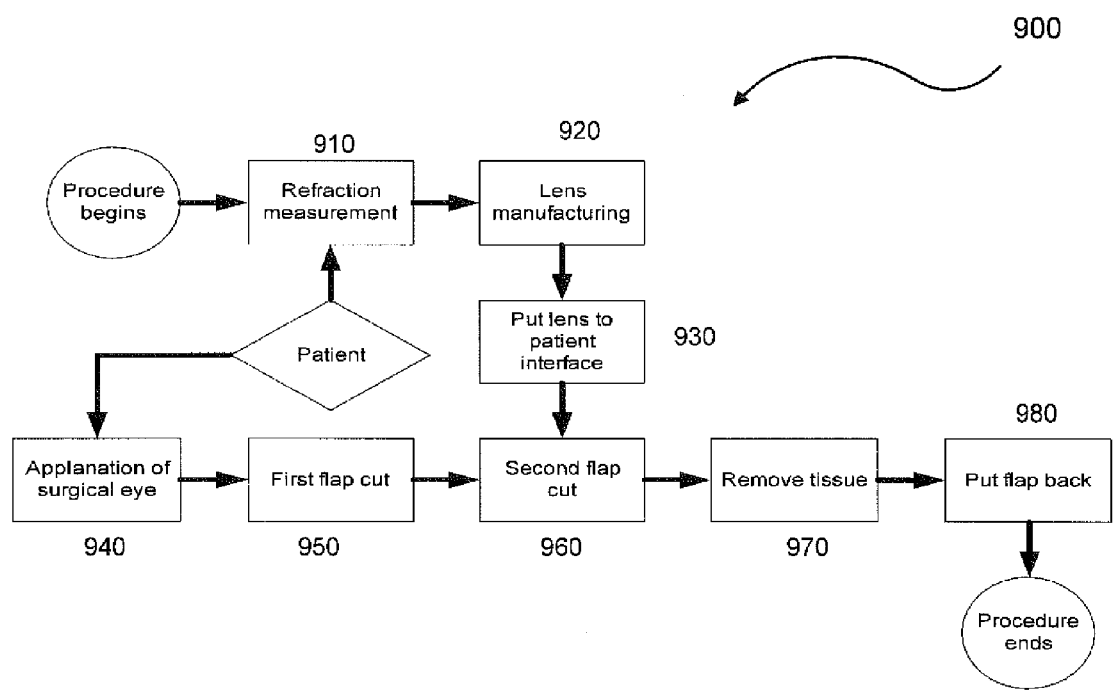
FIG. 9 illustrates diagnostic, manufacturing, and treatment aspects of exemplary methods according to embodiments of the present invention.

FIG. 9 shows a procedural flow chart for deformation mechanism or lens manufacture, as well as patient treatment, according to embodiments of the present invention. Method 900 may include, for example, obtaining a refraction measurement of a patient eye as depicted by step 910. Further, aspects of the process 900 may include manufacturing a lens or deformation mechanism based on the refraction measurement, as depicted by step 920. Lenses, deformation mechanisms, or applanation assembly components can be fabricated using laser ablation processes, and may incorporate standard techniques for the manufacture of intraocular lenses, aspects of which are described in U.S. Pat. Nos. 4,856,234, 5,322,649, and 5,888,122, as well as U.S. Patent Publication No. 2002/0082690. The content of each of these patent publications is incorporated herein by reference. For example, step 920 may include manufacturing a lens according to standard intraocular lens fabrication techniques, such that the shape of the lens is based on measured refractive properties of the eye, and the lens shape corresponds to the refractive correction intended for the eye. Accordingly, when the lens is used in a treatment procedure such as that depicted in FIGS. 1A to 1E (employed as lens 104a, for example), the effect is similar to that of a refractive volumetric ablative resculpting procedure performed with an excimer laser, because both the instant technique and the excimer technique involve cutting or removing an amount of tissue having a certain volume and shape from the eye or corneal stroma. As part of a surgical treatment procedure, aspects of the process may include applanating a patient's eye, or otherwise positioning a corneal deformation mechanism against an anterior surface of the eye of the patient so as to induce a first biomechanical conformation within a corneal stromal tissue of the eye, as depicted by step 940. Further, process 900 may include creating a first flap cut, for example with a femtosecond laser, or otherwise delivering a first photoaltering energy protocol to the eye while the corneal stromal tissue is in the first biomechanical conformation so as to incise the corneal stromal tissue along a first target surface, as depicted by step 950. As shown here, process 900 may also include putting the lens to a patient interface, or otherwise positioning the corneal deformation mechanism against the anterior surface of the eye of the patient, such that the corneal stromal tissue of the eye assumes a second biomechanical conformation different from the first biomechanical conformation, as depicted by step 930. Further, the method 900 may include creating a second flap cut, for example with a femtosecond laser, or otherwise delivering a second photoaltering energy protocol to the eye while the corneal stromal tissue is in the second biomechanical conformation, so as to incise the corneal stromal tissue along a second target surface different from the first target surface, as depicted by step 960. What is more, method 900 may include removing a portion of corneal stromal tissue disposed between the first and second target surfaces or flap cuts, as depicted by step 970. In some cases, removal of the tissue debris or lenticule may include lifting the flap and wiping out the debris or tissue volume using a clinical wiper. In some cases, a phacoemulsification process can be employed and a vacuum can be used to suction out the debris or lenticule without the lifting of the flap, thereby reducing a possible biomechanical effect and induction of high order aberrations. Finally, the method may include putting the flap back or allowing the first and second target surfaces to engage, as depicted by step 980.

Figure 10A:
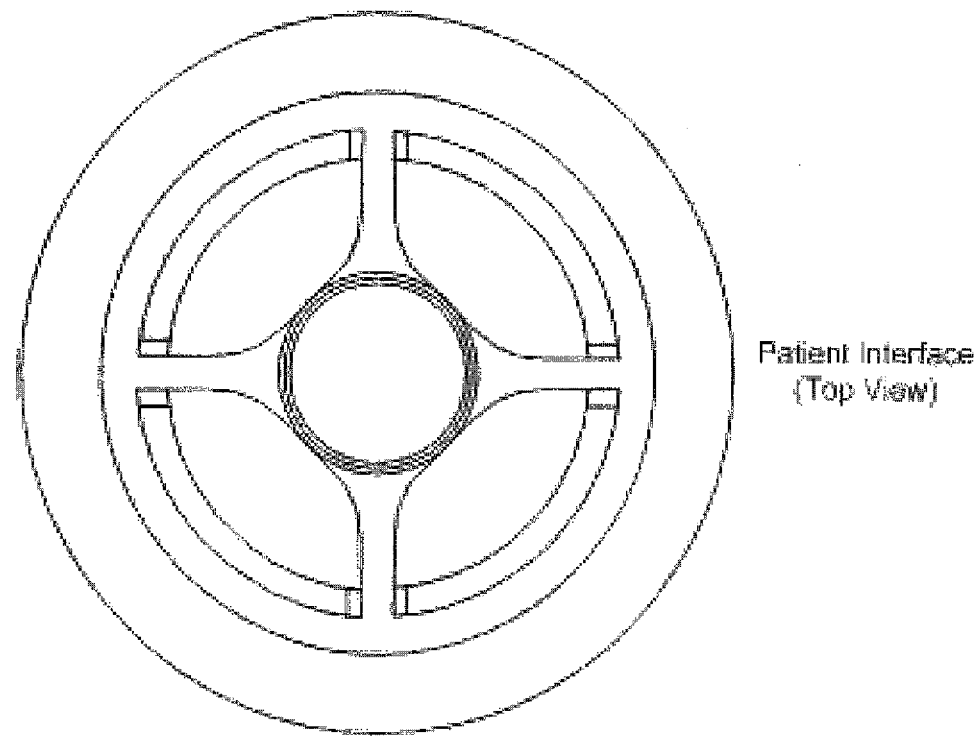
FIGS. 10A and 10B depict aspects of a patient interface according to embodiments of the present invention.
Figure 10B:
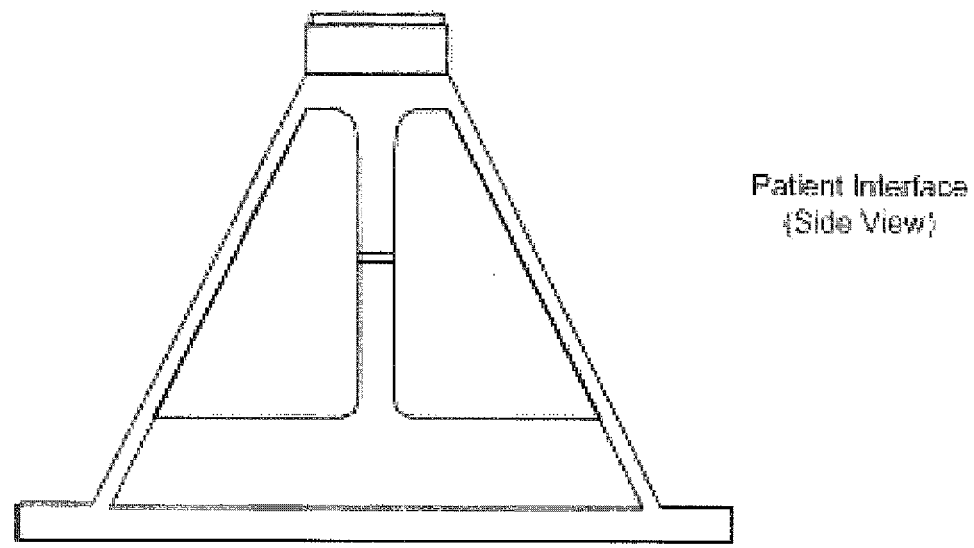
Figure 11A:
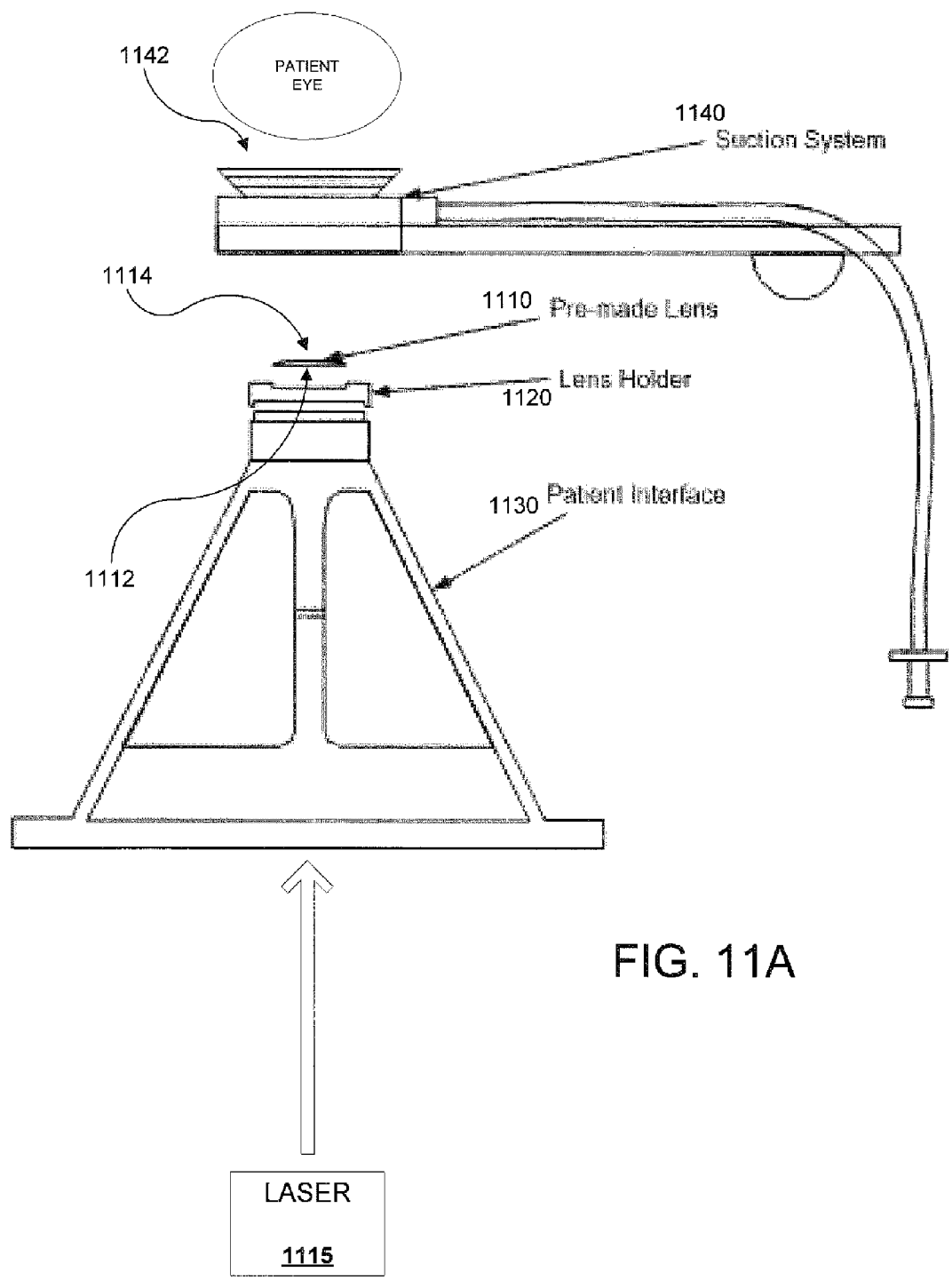

FIGS. 10A and 10B present a top view and a side view, respectively, of a patient interface (PI). As shown in FIG. 11A, in some cases, a pre-made lens or deformation mechanism component 1110 may include a first side 1112 having a flat surface, and a second opposing side 1114 having a curved surface. Accordingly, the flat side 1112 can be fitted into a lens holder 1120 which is created to fit to the patient interface (PI) 1130. In use, the patient interface 1130 can be fit to a suction system 1140, an eye holder 1142 at the top of the suction system 1140, which often includes or can be coupled with a suction or vacuum source, can be pressed to or positioned at the patient surgical eye, and suction can be started, as shown in FIG. 11B. Where the deformation mechanism component or pre-formed lens 1110 incorporates a material with having an index of refraction which approximates that of the eye, femtosecond energy passing through the flat side 1112 and into the eye which is in contact with the opposing side 1114 is therefore not refracted by the lens 1110. In this way, the applied photoalteration energy can provide a precise and exacting fluence so as to create a flat cut (e.g. relative to or parallel with the flat surface 1112. The photoaltered or incised target surface is biomechanically defined by the engagement between the lens (e.g. the curved side 1114) and the cornea. Accordingly, the effect is similar to that of refractive surgery performed with an excimer laser, because both the instant technique and the excimer technique involve cutting or removing an amount of tissue having a certain volume and shape from the eye or corneal stroma.

FIG. 11A depicts the lens 1110, holder 1120, and patient interface 1130, where the patient interface is not fit to the suction system 1140, whereas FIG. 11B shows the suction system 1140 as attached and secured to the patient interface 1130. According to some embodiments, after the suction is initiated or completed, the eye can be applanated and a flap type cut can be performed. During the formation of a first cut or photoalteration, which may be performed with a laser 1115 such as an IntraLase™ femtosecond laser system, a blank block can be used to govern a baseline, in a manner similar to that depicted in FIG. 1B. In some instances, a block or applanation mechanism component 1116 can be cylindrical in shape, or optionally a block, with a height H that is equivalent to the depth D of the lens holder recess 1122, as depicted in FIG. 11C. For the second cut, which can also be formed using laser 1115, the pre-made lens or deformation mechanism 1110 is used in a manner similar to that depicted in FIG. 1C. This way, the first flap cut or photoalteration can provide a an incision surface corresponding to a baseline, and the second flap cut or photoalteration can provide an incision surface corresponding to the profile of the pre-made lens.

According to some embodiments, once the two flap cuts are performed, a phacoemulsification system or technique can be used to sonicate or disrupt the lenticule, and to suction out or aspirate the lenticule or tissue debris from a side hole. In some cases, aspects of this procedure can be programmed in an IntraLase™ system, for example for performance during the first or the second flap cut. This way, the biomechanical effect of flap cuts can be largely reduced. After the bubbles dissipate and the cornea heals, an excimer-like refractive surgery is complete and the eye's vision is treated or corrected.

Figure 12A:
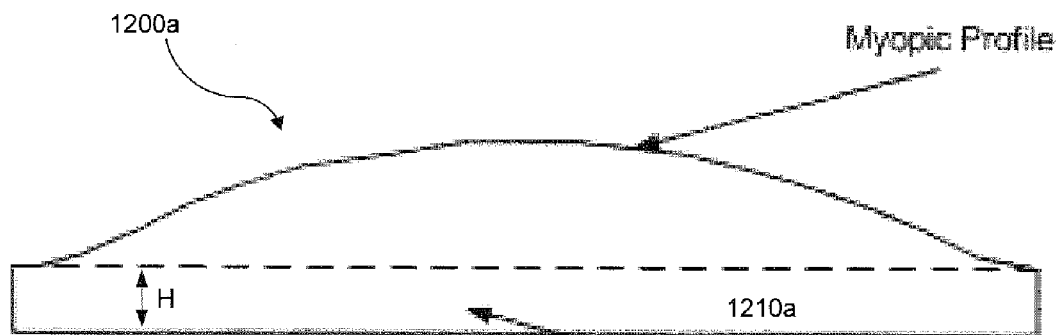
FIGS. 12A and 12B depict aspects of deformation mechanisms according to embodiments of the present invention.
Figure 12B:
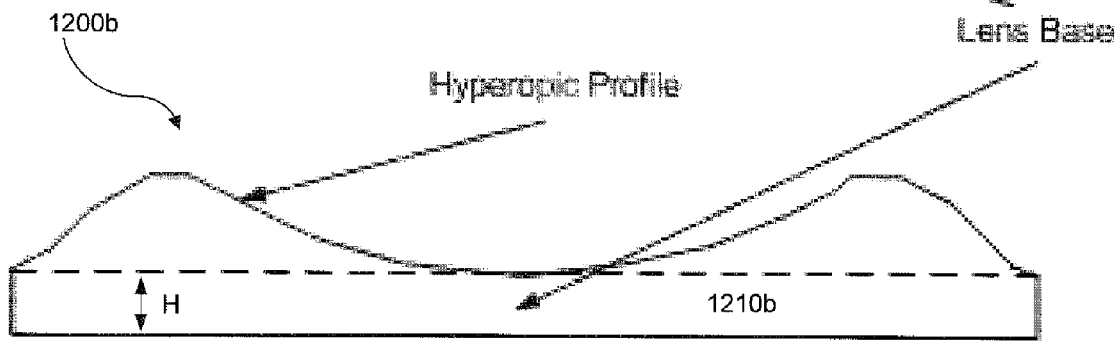

Fabrication or manufacture techniques for a pre-made lens or deformation mechanism may share many similarities with procedures for generating excimer laser ablation targets. For example, FIGS. 12A and 12B show the lens profile of a pre-made lens for a −4 D myopic correction and a +2 D hyperopic correction, respectively. As shown here, the height H of the lens base 1210a, 1210b is identical or substantially similar to the depth of the lens holder, such that the baseline can be correctly defined. For the first flap cut, a glass block or cylinder with the same depth of the lens holder (e.g. as shown in FIG. 11C) can be used. For the second cut, the pre-made lens (e.g. 1200a, 1200b) can be used. The difference of the two cuts (e.g. first photoalteration performed using block or cylinder, second photoalteration performed using pre-made lens) defines the profile or volumetric lenticule to be cut or excised from the eye.

Figure 13A:
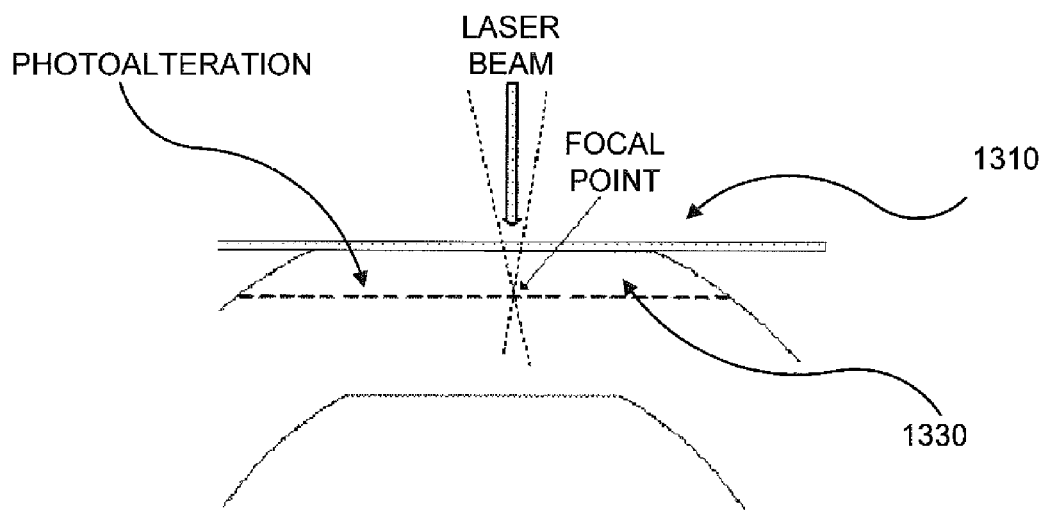
FIGS. 13A and 13B illustrate aspects of treatment processes according to embodiments of the present invention.
Figure 13B:
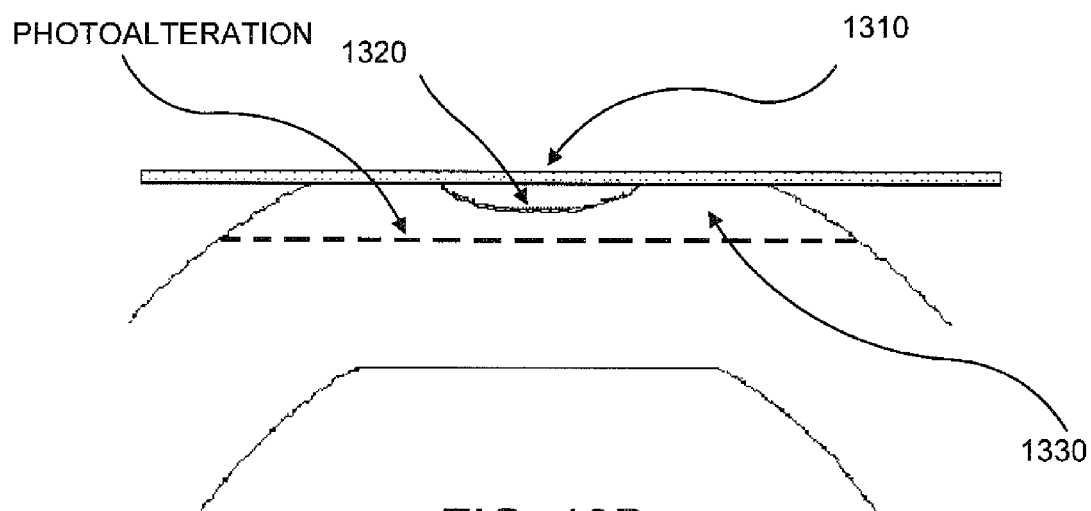

According to some embodiments, as depicted in FIGS. 13A and 13B, a deformation mechanism 1310, which may optionally include or be coupled with a pre-cut lens or auxiliary deformation element 1320, can be used to deform the corneal tissue, and the photoablation can be administered so as to incise and remove an anterior corneal portion 1330, which may include both corneal stroma and epithelium. In this way, embodiments encompass a one-cut photorefractive keratectomy (PRK) technique for laser eye surgery.

Lenses can be fabricated using laser ablation processes, and may incorporate standard techniques for the manufacture of intraocular lenses, aspects of which are described in U.S. Pat. Nos. 4,856,234, 5,322,649, and 5,888,122, as well as U.S. Patent Publication No. 2002/0082690. The content of each of these patent publications is incorporated herein by reference.

According to some embodiments, such profiles can include an optical zone and a transition zone, similar to those provided in excimer-laser refractive surgery techniques. Within the optical zone, the profile can be identical to an excimer-laser ablation profile target.

According to embodiments of the present invention, it is possible to use a lens material with an index of refraction that is not identical to that of the corneal stroma, for example where precise control of the molding of the lens is performed. An advantage of using a lens material with an index of refraction identical or substantially similar to that of the stroma is that it provides for ease of manufacturing of the lens, testing of the lens, and use of existing intraocular lens technologies. For complex shapes, such as wavefront-guided CustomVue™ treatments, a different technology may be used. In this case, it may be desirable to use a lens material that does not have to have identical index of refraction of the stroma. Assuming the index of the refraction of the lens material is $n_m$, and the index of refraction of the stroma is $n_s$, which is 1.377 as commonly used in the industry, the effective optical path difference (OPD) can be adjusted to be:

$$S_n = \frac{n_m - 1}{n_s - 1} S_e \quad (1)$$

Here, $S_n$ is the OPD for the lens, $S_e$ is the OPD for excimer laser, $n_s$ is the index of refraction for stroma, and $n_m$ is the index of refraction for the lens material. For example, when using a lens material with $n_m$=1.5, a −4 D lens can measure at −5.3 D when the lens is profiled. This aspect can be considered during the testing of the lens.

According to some embodiments, systems and methods may involve pre-fabrication of a number of different lenses with different refractive corrections. For a spherical correction (e.g. no cylinder), it can be relatively straightforward, because for every quarter diopter, 4 lenses can be used. Therefore, to cover a refractive range from −12 D to +9 D, it is possible to pre-fabricate 84 such lenses. For a toric lens with cylindrical correction, it is possible to fabricate a lens for a specific refractive power for every 15 degrees of cylindrical correction for every quarter diopter of cylinder, and there can be multiple combinations. Such lenses can be fabricated according to techniques which are used to create intraocular lenses.

As described herein, by employing various combinations of femtosecond laser technology, phacoemulsification techniques, and/or intraocular lens design fabrication processes, it is possible to perform a refractive surgery without the use of an excimer laser.

Embodiments of the present invention further encompass systems and methods for use in cataract surgery procedures, where a cataract or natural lens is removed or treated, but instead of or as a supplement to the introduction of an intraocular or refractive lens, a portion of corneal tissue is removed as described herein. Such techniques may be desirable with, for example, a 4 mm optical zone, the lens having a power of about 20 diopters, optionally in combination with a correction for refractive error of the cornea. In this way, embodiments encompass a lens-less cataract surgery or crystalline lens removal approach to treating the eye of a patient. By providing a machine-implemented treatment within the cornea (e.g. removal of a volume defined by two or more photoalteration surfaces), as opposed to a physician-implemented treatment involving placement of the intraocular lens, procedural efficiencies can be realized.

The methods and apparatuses of the present invention may be provided in one or more kits for such use. The kits may comprise a system for profiling an optical surface, such as an optical surface of an eye, and instructions for use. Optionally, such kits may further include any of the other system components described in relation to the present invention and any other materials or items relevant to the present invention. The instructions for use can set forth any of the methods as described herein.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

What is claimed is:

1. A system for altering refraction of a cornea of an eye of a patient, the system comprising:
    a photoalteration laser for transmitting a laser beam along an optical path;
    a corneal deformation mechanism configured to provide a first applanation shape configuration, and a second applanation shape configuration different from the first applanation shape configuration, the corneal deformation mechanism comprising:
        an applanation plate having a flat proximal portion and a distal portion; wherein the proximal portion is configured to receive the laser beam from the photoalteration laser and the distal portion is configured to engage an anterior corneal surface of the eye so as to induce a first intended biomechanical conformation of reshaping the cornea in the eye in a first profile; and
        a removable body removably attached to the applanation plate;
        wherein the removable body is detached from the applanation plate when the plate is positioned against the cornea in the first profile and attached to the applanation plate when the removable body is positioned against the cornea in a second profile, the removable body having a proximal portion configured to engage the distal portion of the applanation plate and couple the removable body to the applanation plate, and a distal portion configured to engage the anterior corneal surface of the eye so as to induce a second intended biomechanical conformation of reshaping the cornea in the eye in the second profile by altering a depth of focus of the photoalteration laser relative to the anterior corneal surface by deforming the cornea without refracting the photoalteration laser;
    a support for positioning the corneal deformation mechanism along the optical path;
    a processor for determining a first laser target surface based on the first applanation shape configuration and a second laser target surface based on the second applanation shape configuration; wherein the first and second laser target surfaces define a volumetric lenticule that is based on measured refractive properties of the eye and correspond to a desired refractive correction intended for the eye; and
    beam scanning optics coupled to the processor for scanning the laser beam along the first laser target surface when the eye assumes the first intended biomechanical conformation responsive to engagement with the first applanation shape configuration, and along the second laser target surface when the eye assumes the second intended biomechanical conformation responsive to engagement with the second applanation shape configuration.

2. The system according to claim 1, wherein the corneal deformation mechanism comprises a material having an index of refraction similar to a corneal stroma.

3. The system according to claim 1, wherein the distal portion of the applanation plate comprises a flat surface.

4. The system according to claim 1 further comprising a patient interface having a lens holder, the applanation plate configured to fit into the lens holder.

5. The system according to claim 4 further comprising a suction system having an eye holder, the patient interface configured to fit to the suction system.

6. The system according to claim 1, wherein the laser beam has a femtosecond energy with a fluence to create a flat cut parallel to the flat proximal portion of the applanation plate.

* * * * *